(12) United States Patent
Nishimoto

(10) Patent No.: US 8,129,533 B2
(45) Date of Patent: Mar. 6, 2012

(54) METHOD FOR PRODUCTION OF QUINOLONE-CONTAINING LYOPHILIZED PREPARATION

(75) Inventor: Norihiro Nishimoto, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 1008 days.

(21) Appl. No.: 12/067,826

(22) PCT Filed: Sep. 28, 2006

(86) PCT No.: PCT/JP2006/319307
§ 371 (c)(1),
(2), (4) Date: Mar. 24, 2008

(87) PCT Pub. No.: WO2007/037330
PCT Pub. Date: Apr. 5, 2007

(65) Prior Publication Data
US 2008/0300403 A1    Dec. 4, 2008

(30) Foreign Application Priority Data
Sep. 28, 2005 (JP) .................. 2005-282393

(51) Int. Cl.
*C07D 215/38* (2006.01)
(52) U.S. Cl. ........................ 546/159; 546/153
(58) Field of Classification Search .......... 546/153, 546/159
See application file for complete search history.

(56) References Cited

U.S. PATENT DOCUMENTS
2006/0264428 A1    11/2006    Takahashi et al.

FOREIGN PATENT DOCUMENTS

| EP | 0 306 860 A2 | 3/1989 |
|---|---|---|
| EP | 0 306 860 A3 | 3/1989 |
| EP | 0 322 892 A1 | 7/1989 |
| EP | 1 262 477 A1 | 12/2002 |
| EP | 1 336 611 A1 | 8/2003 |
| JP | 57 127406 | 8/1982 |
| JP | 60 178814 | 9/1985 |
| JP | 2003-226643 | 8/2003 |
| WO | 01 58876 | 8/2001 |
| WO | 02 40478 | 5/2002 |
| WO | WO 02/39992 A2 | 5/2002 |
| WO | WO 02/39992 A3 | 5/2002 |
| WO | 2003/066102 * | 8/2003 |
| WO | 2006 123792 | 11/2006 |
| WO | WO 2006/123792 A1 | 11/2006 |

OTHER PUBLICATIONS

Searles, James A. et al., "Annealing to Optimize the Primary Drying Rate, Reduce Freezing-Induced Drying Rate Heterogeneity, and Determine T'g in Pharmaceutical Lyophilization", Journal of Pharmaceutical Sciences, vol. 90, No. 7, pp. 872-887, 2001.

Webb, Serena D. et al., Effects of Annealing Lyophilized and Spray-Lyophilized Formulations of Recombinant Human Interferon-Y, Journal of Pharmaceutical Sciences, vol. 92, No. 4, pp. 715-729, 2003.

Extended European Search Report issued Sep. 15, 2010 in European Patent Application No. 06810754.9.

* cited by examiner

*Primary Examiner* — D M Seaman
(74) *Attorney, Agent, or Firm* — Oblon, Spivak, McClelland, Maier & Neustadt, L.L.P.

(57) ABSTRACT

The present invention is directed to a lyophilized preparation which contains a synthetic quinolone antibacterial compound and, as a solo additive, a pH-adjusting agent, and which exhibits an excellent reconstituting property. The invention provides a method for producing a lyophilized preparation containing a synthetic quinolone antibacterial compound as an active ingredient, characterized by including, sequentially, cooling an aqueous solution containing a synthetic quinolone antibacterial compound and a pH-adjusting agent to yield a frozen product, elevating the temperature of the frozen product, and re-cooling the resultant to prepare the lyophilized preparation.

13 Claims, 7 Drawing Sheets

METHOD FOR PRODUCTION OF QUINOLONE-CONTAINING LYOPHILIZED PREPARATION

CROSS-REFERENCE TO RELATED APPLICATIONS

This application is a 371 of PCT/JP06/319307 filed Sep. 28, 2006 and claims the benefit of JP 2005-282393 filed Sep. 28, 2005.

TECHNICAL FIELD

The present invention relates to a method for producing a lyophilized preparation containing a synthetic quinolone antibacterial compound.

BACKGROUND ART

Synthetic quinolone antibacterial compounds exhibit broad antibacterial spectrum and potent antibacterial activity, and thus have been widely employed as various therapeutic drugs for bacterial infections (see Non-Patent Document 1). Particularly, compounds such as levofloxacin, ofloxacin, ciprofloxacin, moxifloxacin, and trovafloxacin have been widely employed by virtue of excellent antibacterial activity, because of their broad antibacterial spectrum and high antibacterial activity. Similarly, sitafloxacin, a compound represented by formula (I) given hereinbelow, and a compound represented by formula (II) described in the Examples hereinbelow also exhibit excellent antibacterial activity and also exhibit excellent antibacterial activity against drug-resistant bacteria, and thus are promising candidates for excellent antibacterial drugs.

Particularly, a quinolone compound (7-[3-(R)-(1-aminocyclopropyl)pyrrolidin-1-yl]-1-[2-(S)-fluoro-1-(R)-cyclopropyl]-1,4-dihydro-8-methoxy-4-oxoquinoline-3-carboxylic acid) having a structure represented by formula (I) (hereinafter the compound may be abbreviated as "compound (I)"):

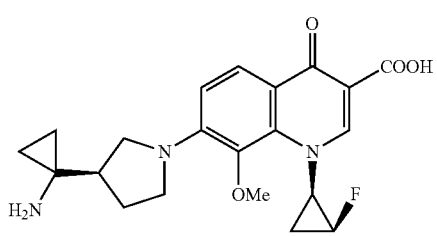

exhibits excellent antibacterial activity; for example, high antibacterial activity against drug-resistant Gram-positive bacteria such as methicillin-resistant staphylococci, penicillin-resistant pneumococci, and vancomycin-resistant enterococci. In addition, compound (I) has high safety, and is expected to exhibit excellent therapeutic effect (see Patent Document 1). Similar to compound (I), compound (II) is an excellent quinolone compound which exhibits excellent antibacterial activity against, for example, drug-resistant bacteria, and has high safety (see Patent Document 2).

Quinolone compounds, particularly those exhibiting excellent antibacterial activity against drug-resistant bacteria, are expected to exhibit excellent therapeutic effects on severe infections by virtue of their antibacterial properties. In many cases, a quinolone compound must be intravascularly administered in the form of solution to patients with severe infections. Therefore, such intravascular administration requires a drug solution containing a quinolone compound; i.e., requires provision of a lyophilized preparation which contains a quinolone compound (i.e., a drug substance) and a pH-adjusting agent as a sole additive, and which is reconstituted upon use.

One known method for preparing a lyophilized preparation includes an annealing step. In the annealing step, the temperature of a frozen product of aqueous raw material solution obtained through a cooling step (i.e., an initial step) is temporarily elevated, and then the solution is maintained for a predetermined period of time. As has been known, a lyophilized preparation which contains an excipient as an additive or as a sole additive and which has been prepared through a method with an annealing step may differ, in terms of reconstituting property, from a lyophilized preparation prepared through a method without annealing step. However, in the above case, the effect of the annealing step does not exhibit a consistent tendency in terms of reconstituting property and actually may be an improving effect or a deteriorating effect. Thus, the effect of the annealing step on reconstituting property of a lyophilized preparation varies depending on a substance contained in the preparation (see Non-Patent Documents 2 and 3).

Intrinsically, a bulking agent is an ingredient for improving the reconstituting property of a lyophilized preparation. The reconstituting property of a lyophilized preparation containing a bulking agent has been known to be affected by an annealing step. However, it has not yet been elucidated the effect of an annealing step on the reconstituting property of a lyophilized preparation which contains no excipient and which has been produced through a method with the annealing step.

Patent Document 1: WO 02/40478
Patent Document 2: Specification of International Application PCT/JP2006/310069
Non-Patent Document 1: Hooper D. C. and Rubinstein E. (eds) 3rd Edition Quinolone Antimicrobial Agents. 2003. ASM Press Books
Non-Patent Document 2: Journal of Pharmaceutical Sciences, Vol. 90, No. 7, pp. 872-887, 2001
Non-Patent Document 3: Journal of Pharmaceutical Sciences, Vol. 92, No. 4, pp. 715-729, 2003

DISCLOSURE OF THE INVENTION

Problems to be Solved by the Invention

A lyophilized preparation containing a synthetic quinolone antibacterial compound such as compound (I) is desirably provided as a preparation containing the compound (i.e., a drug substance) and, as a sole additive, a pH-adjusting agent. As has been elucidated, application of a generally employed lyophilization method to preparation of such a lyophilized preparation may form a hard-to-dissolve lyophilized cake; i.e., a lyophilized cake which requires a long period of time for reconstitution. Specifically, when a liquid for reconstitution is added to such a lyophilized cake for preparing a drug solution, the lyophilized cake does not immediately dissolve in the liquid, and is converted into a hard-to-dissolve lump. Such a hard-to-dissolve lump eventually dissolves completely in the liquid, to thereby yield a drug solution. However, an excessively long period of time for reconstitution results in considerable reduction in convenience of use.

In view of the foregoing, an object of the present invention is to provide a lyophilized preparation which contains a synthetic quinolone antibacterial compound and, as a sole additive, a pH-adjusting agent, and which exhibits an excellent reconstituting property.

Means for Solving the Problems

The present inventor has conducted extensive studies, and as a result has found that when a lyophilized preparation containing a synthetic quinolone antibacterial compound and a pH-adjusting agent as a sole additive is prepared through a method in which an annealing step has been incorporated into a series of freezing steps, the time for reconstitution of the lyophilized preparation is considerably shortened.

Specifically, a lyophilized preparation is produced through a method which comprises: cooling an aqueous solution for the lyophilized preparation containing a synthetic quinolone antibacterial compound and a pH-adjusting agent to yield a frozen product; subjecting the frozen product to a relaxation step, i.e., a step including elevating the temperature of the frozen product and maintaining the temperature for a predetermined period of time; and re-cooling the resultant to prepare the lyophilized preparation. Thus, the inventor's finding is that a lyophilized preparation exhibiting an excellent reconstituting property is produced through a production method to which an annealing step of temporarily elevating the temperature of a frozen product has been added. The present invention has been accomplished on the basis of this finding.

Accordingly, the present invention provides a method for producing a lyophilized preparation containing, as an active ingredient, a compound represented by the following formula (1):

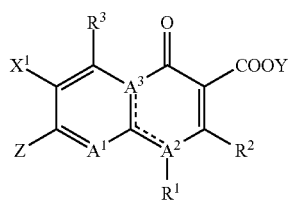

(1)

[wherein $R^1$ represents a C1-C6 alkyl group, a C2-C6 alkenyl group, a C1-C6 halogenoalkyl group, a C3-C6 cycloalkyl group which may be substituted by a halogen atom, an aryl group which may be substituted by a halogen atom, a hydroxyl group, an amino group, a nitro group, a C1-C6 alkyl group, or a C1-C6 alkoxy group, a heteroaryl group which may be substituted by a halogen atom or a C1-C6 alkyl group, a C1-C6 alkoxy group, or a C1-C6 alkylamino group, $R^2$ represents a hydrogen atom or a C1-C6 alkylthio group, wherein $R^1$ and $R^2$ may be linked together to form a ring including a part of the quinolone skeleton, and the ring may contain a sulfur atom as a ring-constituting atom and may have a C1-C6 alkyl group as a substituent, $R^3$ represents a hydrogen atom, an amino group (which may be substituted by a formyl group, a C1-C6 alkyl group, or a C2-C5 acyl group), a thiol group, a halogenomethyl group, a C1-C6 alkyl group, a C2-C6 alkenyl group, a C2-C6 alkynyl group, or a C1-C6 alkoxy group; $A^1$ represents a nitrogen atom or a partial structure represented by formula (2):

(2)

(wherein $X^2$ represents a hydrogen atom, an amino group (which may be substituted by a formyl group, a C1-C6 alkyl group, or a C2-C5 acyl group), a halogen atom, a cyano group, a halogenomethyl group, a halogenomethoxy group, a C1-C6 alkyl group, a C2-C6 alkenyl group, a C2-C6 alkynyl group, or a C1-C6 alkoxy group, wherein $X^2$ and $R^1$ may be linked together to form a ring including a part of the quinolone skeleton, and the ring may contain, as a ring-constituting atom, an oxygen atom, a nitrogen atom, or a sulfur atom and may have a C1-C6 alkyl group as a substituent), each of $A^2$ and $A^3$, which are different from each other, represents a nitrogen atom or a carbon atom, and $A^1$, $A^2$, $A^3$, and the carbon atom bonded thereto form a partial structure represented by the following formula:

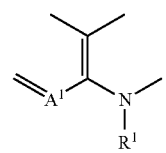

or a partial structure represented by the following formula:

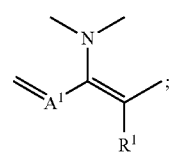

$X^1$ represents a halogen atom or a hydrogen atom, Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidyl group, a 5-alkyl-2-oxo-1,3-dioxol-4-ylmethyl group, a 3-acetoxy-2-oxobutyl group, a C1-C6 alkyl group, a C2-C7 alkoxymethyl group, or a phenylalkyl group consisting of a C1-C6 alkylene group and a phenyl group, Z represents a mono-, di-, or tricyclic heterocyclic substituent, wherein the heterocyclic substituent may be saturated or partially saturated and may contain one or more hetero atoms selected from among a nitrogen atom, an oxygen atom, and a sulfur atom, or the heterocyclic substituent may have a bicyclo structure or a spirocyclic structure and may be substituted by one or more atoms or groups selected from the group consisting of a halogen atom, a hydroxyl group, an amino group, a carbamoyl group, a C1-C6 alkyl group, a C1-C6 halogenoalkyl group, an aryl group, a heteroaryl group, a C1-C6 alkoxy group, a C1-C6 alkylamino group, a C1-C6 alkylthio group, and a C1-C6 aminoalkyl group], characterized in that the method comprises, cooling an aqueous solution containing a compound represented by formula (1) and a pH-adjusting agent to yield a frozen product, elevating the temperature of the frozen product, and re-cooling the resultant to prepare the lyophilized preparation.

EFFECTS OF THE INVENTION

When a lyophilized preparation containing a synthetic quinolone antibacterial compound is prepared through a method with an annealing step, the thus-prepared lyophilized preparation in the form of lyophilized cake exhibits excellent reconstituting property, and improved convenience of use.

BEST MODES FOR CARRYING OUT THE INVENTION

Figure 1:
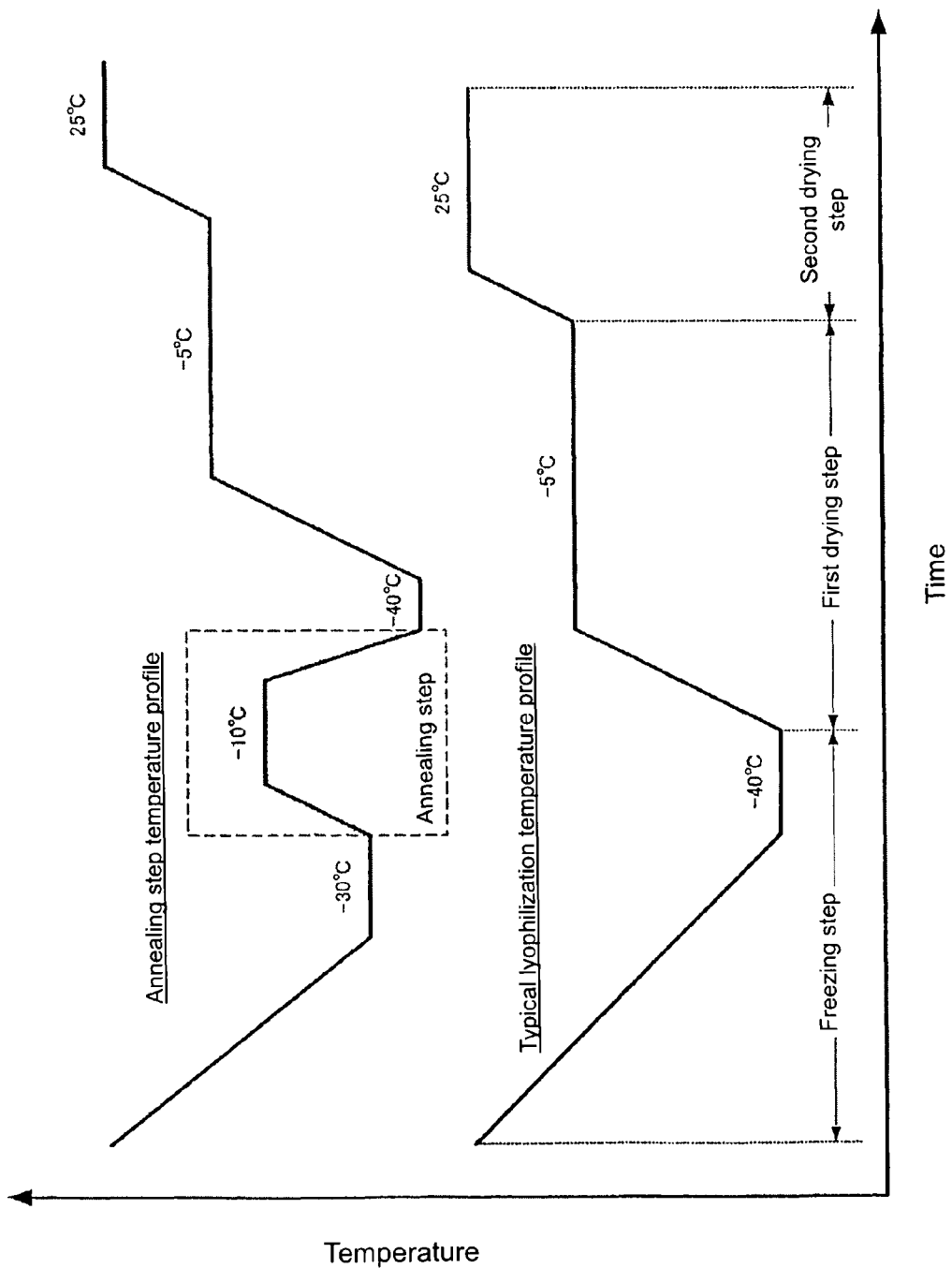
FIG. 1 shows the temperature profiles of a lyophilization method with an annealing step and a lyophilization method without annealing step.

In formula (1), $R^1$ represents a C1-C6 alkyl group; a C2-C6 alkenyl group; a C1-C6 halogenoalkyl group; a C3-C6 cycloalkyl group which may be substituted by a halogen atom; an aryl group which may be substituted by a halogen atom, a hydroxyl group, an amino group, a nitro group, a C1-C6 alkyl group, or a C1-C6 alkoxy group; a heteroaryl group which may be substituted by a halogen atom or a C1-C6 alkyl group; a C1-C6 alkoxy group; or a C1-C6 alkylamino group.

The C1-C6 alkyl group is particularly preferably an ethyl group. The C2-C6 alkenyl group is particularly preferably a vinyl group or a 1-isopropenyl group. The C1-C6 halogenoalkyl group may be a C1-C6 alkyl group having a halogen atom (e.g., fluorine, chlorine, bromine, or iodine), and is particularly preferably a 2-fluoroethyl group. The C3-C6 cycloalkyl group is particularly preferably a cyclopropyl group. When the cycloalkyl group has a substituent, the substituent is preferably a halogen atom, particularly preferably a fluorine atom. A particularly preferred fluorocyclopropyl group is a 2-(S)-fluoro-1-(R)-cyclopropyl group.

The aryl group may be, for example, a phenyl group which may have, as a substituent(s), one to three atoms or groups selected from the group consisting of a halogen atom (e.g., fluorine, chlorine, or bromine), a hydroxyl group, an amino group, a nitro group, a C1-C6 alkyl group, and a C1-C6 alkoxy group. The aryl group is preferably a phenyl group, a 2-fluorophenyl group, a 4-fluorophenyl group, a 2,4-difluorophenyl group, a 2-fluoro-4-hydroxyphenyl group, a 3-amino-4,6-difluorophenyl group, or a 4,6-difluoro-3-methylaminophenyl group.

The heteroaryl group may be an aromatic heterocyclic substituent which is derived from a 5- or 6-membered aromatic heterocyclic compound, and which may have, as a substituent, a halogen atom or a C1-C6 alkyl group. The heteroaryl group contains one or more hetero atoms selected from among a nitrogen atom, an oxygen atom, and a sulfur atom. The heteroaryl group may be, for example, a pyridyl group or a pyrimidyl group, and is particularly preferably a 6-amino-3,5-difluoro-2-pyridyl group.

The C1-C6 alkoxy group is particularly preferably a methoxy group. The C1-C6 alkylamino group is particularly preferably a methylamino group.

The substituent $R^1$ is preferably a cycloalkyl group or a halogenocycloalkyl group. The cycloalkyl group is particularly preferably a cyclopropyl group. A halogenocyclopropyl group is preferably a 2-halogenocyclopropyl group, particularly preferably a 2-fluorocyclopropyl group.

In formula (1), $R^2$ represents a hydrogen atom or a C1-C6 alkylthio group. The C1-C6 alkylthio group is particularly preferably a methylthio group or an ethylthio group.

The substituent $R^2$ is preferably a hydrogen atom.

In formula (1), $R^1$ and $R^2$ may be linked together to form a ring including a part of the quinolone skeleton. The thus-formed ring may contain a sulfur atom as a ring-constituting atom, and the ring may have a C1-C6 alkyl group as a substituent. The alkyl group is preferably a methyl group.

In formula (1), $R^3$ represents a hydrogen atom, an amino group (which may be substituted by a formyl group, a C1-C6 alkyl group, or a C2-C5 acyl group), a thiol group, a halogenomethyl group, a C1-C6 alkyl group, a C2-C6 alkenyl group, a C2-C6 alkynyl group, or a C1-C6 alkoxy group.

The amino group which may be substituted by a formyl group, a C1-C6 alkyl group, or a C2-C5 acyl group may be, for example, a formylamino group or an acetylamino group, and is particularly preferably an acetylamino group. The C1-C6 alkyl group may be a methyl group or an ethyl group, and is particularly preferably a methyl group. The C2-C6 alkenyl group is particularly preferably a vinyl group. The C2-C6 alkynyl group is particularly preferably an ethynyl group. The C1-C6 alkoxy group is particularly preferably a methoxy group.

The substituent $R^3$ is preferably a hydrogen atom.

In formula (1), $A^1$ represents a nitrogen atom or a partial structure represented by formula (2).

(2)

In formula (2), $X^2$ represents a hydrogen atom, an amino group (which may be substituted by a formyl group, a C1-C6 alkyl group, or a C2-C5 acyl group), a halogen atom, a cyano group, a halogenomethyl group, a halogenomethoxy group, a C1-C6 alkyl group, a C2-C6 alkenyl group, a C2-C6 alkynyl group, or a C1-C6 alkoxy group.

The amino group which may be substituted by a formyl group, a C1-C6 alkyl group, or a C2-C5 acyl group is particularly preferably an acetylamino group. The C1-C6 alkyl group is particularly preferably a methyl group. The C2-C6 alkenyl group is particularly preferably a vinyl group. The C2-C6 alkynyl group is particularly preferably an ethynyl group. The C1-C6 alkoxy group is particularly preferably a methoxy group.

$X^2$ and the aforementioned $R^1$ may be linked together to form a ring including a part of the quinolone skeleton, and the thus-formed ring may contain, as a ring-constituting atom, an oxygen atom, a nitrogen atom, or a sulfur atom. The ring may have a C1-C6 alkyl group as a substituent.

The thus-formed ring structure is preferably a pyridobenzoxazine skeleton, which is a skeleton of, for example, ofloxacin. The alkyl substituent of this skeleton is preferably a methyl group, particularly preferably a (3S)-methyl group.

The substituent $A^1$ is preferably a partial structure represented by formula (2), and the substituent $X^2$ is preferably a methyl group, a methoxy group, or a difluoromethoxy group.

In formula (1), each of $A^2$ and $A^3$, which are different from each other, represents a nitrogen atom or a carbon atom. $A^1$, $A^2$, $A^3$, and the carbon atom bonded thereto form a partial structure represented by the following formula:

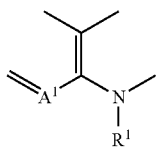

or a partial structure represented by the following formula.

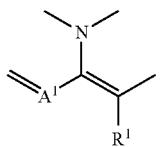

Of these partial structures, the partial structure represented by the following formula:

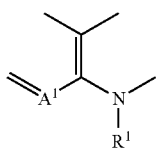

is preferred.

In formula (1), $X^1$ represents a halogen atom or a hydrogen atom. When $X^1$ is a halogen atom, the halogen atom is preferably fluorine.

The substituent $X^1$ is preferably a fluorine atom or a hydrogen atom.

In formula (1), Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidyl group, a 5-alkyl-2-oxo-1,3-dioxol-4-ylmethyl group, a 3-acetoxy-2-oxobutyl group, a C1-C6 alkyl group, a C2-C7 alkoxymethyl group, or a phenylalkyl group consisting of a C1-C6 alkylene group and a phenyl group.

The substituent Y is preferably a hydrogen atom.

In formula (1), Z represents a mono-, di-, or tricyclic heterocyclic substituent. The heterocyclic substituent may be saturated or partially saturated, and may contain one or more hetero atoms selected from among a nitrogen atom, an oxygen atom, and a sulfur atom. The heterocyclic substituent may have a bicyclo structure or a spirocyclic structure. The heterocyclic substituent may have a substituent, and may be substituted by, for example, a halogen atom, a hydroxyl group, an amino group, a carbamoyl group, a C1-C6 alkyl group, a C1-C6 halogenoalkyl group, an aryl group, a heteroaryl group, a C1-C6 alkoxy group, a C1-C6 alkylamino group, a C1-C6 alkylthio group, or a C1-C6 aminoalkyl group. The heterocyclic substituent may be substituted by one atom or group, or two or more atoms or groups.

The C1-C6 alkyl group which may serve as a substituent of the aforementioned heterocyclic substituent may have, as a substituent(s), one or more atoms or groups selected from the group consisting of a halogen atom, a hydroxyl group, an amino group, a carbamoyl group, a C1-C6 halogenoalkyl group, a C1-C6 alkoxy group, a C1-C6 alkylamino group, a C1-C6 alkylthio group, and a C1-C6 aminoalkyl group. The alkyl group which may serve as a substituent of the heterocyclic substituent, or the alkyl moiety of the halogenoalkyl group, alkylamino group, alkylthio group, or aminoalkyl group which may serve as a substituent of the alkyl group may have a cyclic structure, and may have, as a substituent(s), one or more atoms or groups selected from the group consisting of a halogen atom, a C1-C6 alkyl group, and a C1-C6 alkoxy group.

The amino moiety of the aforementioned amino group, alkylamino group, or aminoalkyl group may have, as a substituent(s), one or two C1-C6 alkyl groups (which may have a cyclic structure, and may have, as a substituent(s), one or more atoms or groups selected from the group consisting of a hydroxyl group, a halogen atom, a C1-C6 alkylthio group, and a C1-C6 alkoxy group). When the amino moiety has two C1-C6 alkyl groups, they may be identical to or different from each other. The amino moiety may be protected by a generally employed protective group.

The alkyl moiety of the C1-C6 halogenoalkyl group, C1-C6 alkylamino group, C1-C6 alkylthio group, or C1-C6 aminoalkyl group which may serve as a substituent of the aforementioned heterocyclic substituent may have a cyclic structure, and may have, as a substituent(s), one or more atoms or groups selected from the group consisting of a halogen atom, a C1-C6 alkyl group, a C1-C6 alkoxy group, an aryl group, and a heteroaryl group.

The amino moiety of the amino group, C1-C6 alkylamino group, or C1-C6 aminoalkyl group which may serve as a substituent of the aforementioned heterocyclic substituent may have, as a substituent(s), one or two C1-C6 alkyl groups, or may be protected by a protective group. When the amino moiety has two C1-C6 alkyl groups, they may be identical to or different from each other.

The C1-C6 alkyl group may have a cyclic structure, and may have, as a substituent(s), one or more atoms or groups selected from the group consisting of a halogen atom, a hydroxyl group, a C1-C6 alkylthio group, and a C1-C6 alkoxy group.

No particular limitation is imposed on the amino protective group, so long as it is generally employed in the art. Examples of the amino protective group which may be employed include alkoxycarbonyl groups such as tert-butoxycarbonyl and 2,2,2-trichloroethoxycarbonyl; aralkyloxycarbonyl groups such as benzyloxycarbonyl, p-methoxybenzyloxycarbonyl, and p-nitrobenzyloxycarbonyl; acyl groups such as acetyl, methoxyacetyl, trifluoroacetyl, chloroacetyl, pivaloyl, formyl, and benzoyl; alkyl groups and aralkyl groups such as tert-butyl, benzyl, p-nitrobenzyl, p-methoxybenzyl, and triphenylmethyl; ether groups such as methoxymethyl, tert-butoxymethyl, tetrahydropyranyl, and 2,2,2-trichloroethoxymethyl; and (alkyl and/or aralkyl)-substituted silyl groups such as trimethylsilyl, isopropyldimethylsilyl, tert-butyldimethylsilyl, tribenzylsilyl, and tert-butyldiphenylsilyl.

The aryl group which may serve as a substituent of the aforementioned heterocyclic substituent has 6 to 10 carbon atoms. The heteroaryl group which may serve as a substituent of the heterocyclic substituent is a 5- or 6-membered ring, and may contain one to four hetero atoms selected from among a nitrogen atom, an oxygen atom, and a sulfur atom.

The aryl group or heteroaryl group which may serve as a substituent of the aforementioned heterocyclic substituent may have, as a substituent(s), one or more atoms or groups selected from the group consisting of a halogen atom, a hydroxyl group, a thiol group, an amino group, a nitro group, a cyano group, a carboxyl group, a carbamoyl group, a phenyl group, a C1-C6 alkyl group, a C1-C6 alkoxy group, a C1-C6 alkylthio group, a C2-C6 alkoxycarbonyl group, a C2-C5 acyl group, and a heteroaryl group (which is a 5- or 6-membered ring, and contains one to four hetero atoms selected from among a nitrogen atom, an oxygen atom, and a sulfur atom).

The phenyl group, C1-C6 alkyl group, C1-C6 alkoxy group, C1-C6 alkylthio group, C2-C6 alkoxycarbonyl group, C2-C5 acyl group, or heteroaryl group which may serve as a substituent of the aforementioned aryl group or heteroaryl group may have, as a substituent(s), one or more atoms or groups selected from the group consisting of a halogen atom, a hydroxyl group, a C1-C6 alkoxy group, and a C1-C6 alkylthio group. The amino group which may serve as a substituent of the aryl group or heteroaryl group may have, as a substituent(s), one or two groups selected from the group consisting of a formyl group, a C1-C6 alkyl group, a C2-C5 acyl group, and a C2-C5 alkoxycarbonyl group.

The substituent Z may be bonded to the quinolone skeleton via any of the atoms constituting the ring of the substituent, but is preferably bonded to the quinolone skeleton via a nitrogen atom. Examples of such a heterocyclic substituent bonded to the quinolone skeleton via a nitrogen atom include substituents having structures represented by the following formulas (3) to (7):

a structure represented by formula (3):

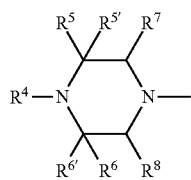

(3)

(wherein each of $R^4$, $R^5$, $R^{5'}$, $R^6$, $R^{6'}$, $R^7$, and $R^8$ represents a substituent of any of the aforementioned heterocyclic substituents represented by Z; more specifically, each of $R^4$, $R^5$, and $R^6$ independently represents a hydrogen atom or a C1-C6 alkyl group, wherein the alkyl group may have, as a substituent(s), one or more groups selected from the group consisting of a halogen atom, a hydroxyl group, an amino group, a carbamoyl group, a C1-C6 alkylthio group, a C1-C6 alkoxy group, a C1-C6 alkylamino group, a C1-C6 halogenoalkyl group, and a C1-C6 aminoalkyl group;

the aforementioned alkyl group, or the alkyl moiety of the alkylthio group, alkylamino group, halogenoalkyl group, or aminoalkyl group which may serve as a substituent of the alkyl group may have a cyclic structure, and may have, as a substituent(s), one or more atoms or groups selected from the group consisting of a halogen atom, a C1-C6 alkyl group, and an alkoxy group; and the amino moiety of the amino group, aminoalkyl group, or alkylamino group which may serve as a substituent of the alkyl group may have, as a substituent(s), one or two C1-C6 alkyl groups (which may have a cyclic structure, and may have, as a substituent(s), one or more atoms or groups selected from the group consisting of a halogen atom, a hydroxyl group, a C1-C6 alkylthio group, and a C1-C6 alkoxy group) (when the amino moiety has two C1-C6 alkyl groups, they may be identical to or different from each other), and the amino moiety may be protected by a generally employed protective group;

each of $R^{5'}$ and $R^{6'}$ independently represents a hydrogen atom, an aryl group, or a heteroaryl group, wherein the aryl group has 6 to 10 carbon atoms, and the heteroaryl group is a 5- or 6-membered ring, and may contain one to four hetero atoms arbitrarily selected from among a nitrogen atom, an oxygen atom, and a sulfur atom;

the aforementioned aryl group or heteroaryl group may have, as a substituent(s), one or more atoms or groups selected from the group consisting of a halogen atom, a hydroxyl group, a thiol group, an amino group, a nitro group, a cyano group, a carboxyl group, a carbamoyl group, a phenyl group, a C1-C6 alkyl group, a C1-C6 alkoxy group, a C1-C6 alkylthio group, a C2-C6 alkoxycarbonyl group, a C2-C5 acyl group, and a heteroaryl group (which is a 5- or 6-membered ring, and contains one to four hetero atoms arbitrarily selected from among a nitrogen atom, an oxygen atom, and a sulfur atom); and of these substituents, the alkyl group, alkoxy group, alkylthio group, alkoxycarbonyl group, acyl group, phenyl group, or heteroaryl group may have, as a substituent(s), one or more atoms or groups selected from the group consisting of a halogen atom, a hydroxyl group, a C1-C6 alkoxy group, and a C1-C6 alkylthio group, and the amino group may have, as a substituent(s), one or two groups selected from the group consisting of a formyl group, a C1-C6 alkyl group, a C2-C5 acyl group, and a C2-C5 alkoxycarbonyl group; and each of $R^7$ and $R^8$ independently represents a hydrogen atom or a C1-C6 alkyl group, wherein two substituents arbitrarily selected from among $R^5$, $R^{5'}$, $R^6$, and $R^{6'}$ may together form a ring, and the thus-formed ring may contain, as a ring-constituting atom(s), one or more hetero atoms arbitrarily selected from among an oxygen atom, a nitrogen atom, and a sulfur atom; and the thus-formed ring may have, as a substituent(s), one or more atoms or groups selected from the group consisting of a halogen atom, a hydroxyl group, an amino group, a C1-C6 alkyl group, a C1-C6 alkoxy group, and a C1-C6 alkylthio group, and the amino group may have, as a substituent(s), one or two groups selected from the group consisting of a formyl group, a C1-C6 alkyl group, a C2-C5 acyl group, and a C2-C5 alkoxycarbonyl group);

or a structure represented by formula (4):

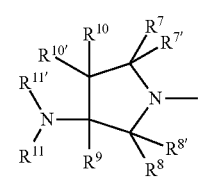

(4)

(wherein each of $R^7$, $R^{7'}$, $R^8$, $R^{8'}$, $R^9$, $R^{10}$, $R^{10'}$, $R^{11}$, and $R^{11'}$ represents a substituent on any of the aforementioned heterocyclic substituents represented by Z; more specifically, each of $R^{11}$ and $R^{11'}$ independently represents a hydrogen atom or a C1-C6 alkyl group, wherein the alkyl group may have, as a substituent(s), one or more atoms or groups selected from the group consisting of a halogen atom, a hydroxyl group, an amino group, a carbamoyl group, a C1-C6 alkylthio group, a C1-C6 alkoxy group, a C1-C6 alkylamino group, a C1-C6 halogenoalkyl group, and a C1-C6 aminoalkyl group;

each of $R^9$, $R^{10}$, and $R^{10'}$ independently represents a hydrogen atom, a halogen atom, an amino group, a hydroxyl group, a carbamoyl group, a C1-C6 alkyl group, a C1-C6 alkylamino group, an aryl group, a heteroaryl group, a C1-C6 alkoxy group, a C1-C6 alkylthio group, a C1-C6 halogenoalkyl group, or a C1-C6 aminoalkyl group, wherein the alkyl group, or the alkyl moiety of the alkylthio group, halogenoalkyl group, aminoalkyl group, or alkylamino group may have a cyclic structure, and may have, as a substituent(s), one or more atoms or groups selected from the group consisting of a halogen atom, a C1-C6 alkyl group, and a C1-C6 alkoxy group;

the amino moiety of the aforementioned amino group, alkylamino group, or aminoalkyl group may have, as a substituent(s), one or two C1-C6 alkyl groups (which may have a cyclic structure, and may have, as a substituent(s), one or more atoms or groups selected from the group consisting of a halogen atom, a hydroxyl group, a C1-C6 alkylthio group, and a C1-C6 alkoxy group) (when the amino moiety has two C1-C6 alkyl groups, they may be identical to or different from each other), and the amino moiety may be protected by a generally employed protective group;

the aforementioned aryl group has 6 to 10 carbon atoms, and the heteroaryl group is a 5- or 6-membered ring, and may contain one to four hetero atoms arbitrarily selected from among a nitrogen atom, an oxygen atom, and a sulfur atom;

the aforementioned aryl group or heteroaryl group may have, as a substituent(s), one or more atoms or groups selected from the group consisting of a halogen atom, a hydroxyl group, a thiol group, an amino group, a nitro group, a cyano group, a carboxyl group, a carbamoyl group, a phenyl group, a C1-C6 alkyl group, a C1-C6 alkoxy group, a C1-C6 alkylthio group, a C2-C6 alkoxycarbonyl group, a C2-C5 acyl group, and a heteroaryl group (which is a 5- or 6-membered ring, and contains one to four hetero atoms arbitrarily selected from among a nitrogen atom, an oxygen atom, and a sulfur atom); and of these substituents, the alkyl group, alkoxy group, alkylthio group, alkoxycarbonyl group, acyl group, phenyl group, or heteroaryl group may have, as a substituent(s), one or more atoms or groups selected from the group consisting of a halogen atom, a hydroxyl group, a C1-C6 alkoxy group, and a C1-C6 alkylthio group, and the amino group may have, as a substituent(s), one or two groups selected from the group consisting of a formyl group, a C1-C6 alkyl group, a C2-C5 acyl group, and a C2-C5 alkoxycarbonyl group; and each of $R^7$, $R^{7'}$, $R^8$, and $R^{8'}$ independently represents a hydrogen atom or a C1-C6 alkyl group;

two substituents arbitrarily selected from among $R^7$, $R^{7'}$, $R^8$, $R^{8'}$, $R^9$, $R^{10}$, and $R^{10'}$ may together form a ring, and the thus-formed ring may contain, as a ring-constituting atom(s), one or more hetero atoms arbitrarily selected from among an oxygen atom, a nitrogen atom, and a sulfur atom; and the thus-formed ring may have, as a substituent(s), one or more atoms or groups selected from the group consisting of a halogen atom, a hydroxyl group, an amino group, a C1-C6 alkyl group, a C1-C6 alkoxy group, and a C1-C6 alkylthio group, and the amino group may have, as a substituent(s), one or two groups selected from the group consisting of a formyl group, a C1-C6 alkyl group, a C2-C5 acyl group, and a C2-C5 alkoxycarbonyl group);

or a structure represented by formula (5):

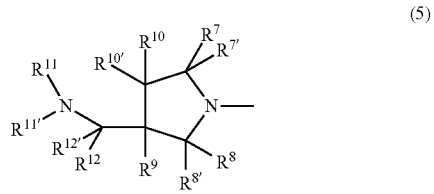

(5)

(wherein each of $R^7$, $R^{7'}$, $R^8$, $R^{8'}$, $R^9$, $R^{10}$, $R^{10'}$, $R^{11}$, $R^{11'}$, $R^{12}$, and $R^{12'}$ represents a substituent on any of the aforementioned heterocyclic substituents represented by Z; more specifically, each of $R^{11}$ and $R^{11'}$ independently represents a hydrogen atom or a C1-C6 alkyl group, wherein the alkyl group may have, as a substituent(s), one or more atoms or groups selected from the group consisting of a halogen atom, a hydroxyl group, an amino group, a carbamoyl group, a C1-C6 alkylthio group, a C1-C6 alkoxy group, a C1-C6 alkylamino group, a C1-C6 halogenoalkyl group, and a C1-C6 aminoalkyl group;

each of $R^9$, $R^{10}$, and $R^{10'}$ independently represents a hydrogen atom, a halogen atom, a hydroxyl group, an amino group, a carbamoyl group, a C1-C6 alkyl group, a C1-C6 alkylamino group, an aryl group, a heteroaryl group, a C1-C6 alkoxy group, a C1-C6 alkylthio group, a C1-C6 halogenoalkyl group, or a C1-C6 aminoalkyl group, wherein the aforementioned alkyl group, or the alkyl moiety of the alkylthio group, halogenoalkyl group, aminoalkyl group, or alkylamino group may have a cyclic structure, and may have, as a substituent(s), one or more atoms or groups selected from the group consisting of a halogen atom, a C1-C6 alkyl group, and a C1-C6 alkoxy group; and the amino moiety of the aforementioned amino group, alkylamino group, or aminoalkyl group may have, as a substituent(s), one or two C1-C6 alkyl groups (which may have a cyclic structure, and may have, as a substituent(s), one or more atoms or groups selected from the group consisting of a halogen atom, a hydroxyl group, a C1-C6 alkylthio group, and a C1-C6 alkoxy group) (when the amino moiety has two C1-C6 alkyl groups, they may be identical to or different from each other), and the amino moiety may be protected by a generally employed protective group;

each of $R^{12}$ and $R^{12'}$ independently represents a hydrogen atom, a C1-C6 alkyl group, an aryl group, or a heteroaryl group, wherein the aryl group has 6 to 10 carbon atoms, and the heteroaryl group is a 5- or 6-membered ring, and may contain one to four hetero atoms arbitrarily selected from among a nitrogen atom, an oxygen atom, and a sulfur atom;

the aforementioned aryl group or heteroaryl group may have, as a substituent(s), one or more atoms or groups selected from the group consisting of a halogen atom, a hydroxyl group, a thiol group, an amino group, a nitro group, a cyano group, a carboxyl group, a carbamoyl group, a phenyl group, a C1-C6 alkyl group, a C1-C6 alkoxy group, a C1-C6 alkylthio group, a C2-C6 alkoxycarbonyl group, a C2-C5 acyl group, and a heteroaryl group (which is a 5- or 6-membered ring, and contains one to four hetero atoms arbitrarily selected from among a nitrogen atom, an oxygen atom, and a sulfur atom); and of these substituents, the alkyl group, alkoxy group, alkylthio group, alkoxycarbonyl group, acyl group, phenyl group, or heteroaryl group may have, as a substituent(s), one or more atoms or groups selected from the group consisting of a halogen atom, a hydroxyl group, a C1-C6 alkoxy group, and a C1-C6 alkylthio group, and the amino group may have, as a substituent(s), one or two groups selected from the group consisting of a formyl group, a C1-C6 alkyl group, a C2-C5 acyl group, and a C2-C5 alkoxycarbonyl group; and each of $R^7$, $R^{7'}$, $R^8$, and $R^{8'}$ independently represents a hydrogen atom or a C1-C6 alkyl group, wherein two substituents arbitrarily selected from among $R^7$, $R^{7'}$, $R^8$, $R^{8'}$, $R^9$, $R^{10}$, $R^{10'}$, $R^{12}$, and $R^{12'}$ may together form a ring, and the thus-formed ring may contain, as a ring-constituting atom(s), one or more hetero atoms arbitrarily selected from among an oxygen atom, a nitrogen atom, and a sulfur atom; and the thus-formed ring may have, as a substituent(s), one or more atoms or groups selected from the group consisting of a halogen atom, a hydroxyl group, an amino group, a C1-C6 alkyl group, a C1-C6 alkoxy group, and a C1-C6 alkylthio group, and the amino group may have, as a substituent(s), one or two groups selected from the group consisting of a formyl group, a C1-C6 alkyl group, a C2-C5 acyl group, and a C2-C5 alkoxycarbonyl group);

or a structure represented by formula (6):

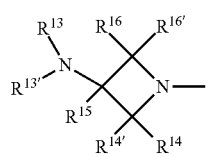

(6)

(wherein each of $R^{13}$, $R^{13'}$, $R^{14}$, $R^{14'}$, $R^{15}$, $R^{16}$, and $R^{16'}$ represents a substituent on any of the aforementioned heterocyclic substituents represented by Z; more specifically, each of $R^{13}$ and $R^{13'}$ independently represents a hydrogen atom or a C1-C6 alkyl group, wherein the alkyl group may have, as a substituent(s), one or more atoms or groups selected from the group consisting of a halogen atom, a hydroxyl group, an amino group, a carbamoyl group, a C1-C6 alkylthio group, a C1-C6 alkoxy group, a C1-C6 alkylamino group, a C1-C6 halogenoalkyl group, and a C1-C6 aminoalkyl group; and each of $R^{14}$, $R^{14'}$, $R^{15}$, $R^{16}$, and $R^{16'}$ independently represents a hydrogen atom, a halogen atom, a hydroxyl group, an amino group, a carbamoyl group, a C1-C6 alkyl group, a C1-C6 alkylamino group, an aryl group, a heteroaryl group, a C1-C6 alkoxy group, a C1-C6 alkylthio group, a C1-C6 halogenoalkyl group, or a C1-C6 aminoalkyl group, wherein the aforementioned alkyl group, or the alkyl moiety of the alkylthio group, halogenoalkyl group, aminoalkyl group, or alkylamino group may have a cyclic structure, and may have, as a substituent(s), one or more atoms or groups selected from the group consisting of a halogen atom, a C1-C6 alkyl group, and a C1-C6 alkoxy group;

the amino moiety of the aforementioned amino group, aminoalkyl group, or alkylamino group may have, as a substituent(s), one or two C1-C6 alkyl groups (which may have a cyclic structure, and may have, as a substituent(s), one or more atoms or groups selected from the group consisting of a halogen atom, a hydroxyl group, a C1-C6 alkylthio group, and a C1-C6 alkoxy group) (when the amino moiety has two C1-C6 alkyl groups, they may be identical to or different from each other), and the amino moiety may be protected by a generally employed protective group;

the aforementioned aryl group has 6 to 10 carbon atoms, and the heteroaryl group is a 5- or 6-membered ring, and may contain one to four hetero atoms arbitrarily selected from among a nitrogen atom, an oxygen atom, and a sulfur atom;

the aforementioned aryl group or heteroaryl group may have, as a substituent(s), one or more atoms or groups selected from the group consisting of a halogen atom, a hydroxyl group, a thiol group, an amino group, a nitro group, a cyano group, a carboxyl group, a carbamoyl group, a phenyl group, a C1-C6 alkyl group, a C1-C6 alkoxy group, a C1-C6 alkylthio group, a C2-C6 alkoxycarbonyl group, a C2-C5 acyl group, and a heteroaryl group (which is a 5- or 6-membered ring, and contains one to four hetero atoms arbitrarily selected from among a nitrogen atom, an oxygen atom, and a sulfur atom);

of these substituents, the alkyl group, alkoxy group, alkylthio group, alkoxycarbonyl group, acyl group, phenyl group, or heteroaryl group may have, as a substituent(s), one or more atoms or groups selected from the group consisting of a halogen atom, a hydroxyl group, a C1-C6 alkoxy group, and a C1-C6 alkylthio group, and the amino group may have, as a substituent(s), one or two groups selected from the group consisting of a formyl group, a C1-C6 alkyl group, a C2-C5 acyl group, and a C2-C5 alkoxycarbonyl group;

two substituents arbitrarily selected from among $R^{14}$, $R^{14'}$, $R^{15}$, $R^{16}$, and $R^{16'}$ may together form a ring, and the thus-formed ring may contain, as a ring-constituting atom(s), one or more hetero atoms arbitrarily selected from among an oxygen atom, a nitrogen atom, and a sulfur atom; and the thus-formed ring may have, as a substituent(s), one or more atoms or groups selected from the group consisting of a halogen atom, a hydroxyl group, an amino group, a C1-C6 alkyl group, a C1-C6 alkoxy group, and a C1-C6 alkylthio group, and the amino group may have, as a substituent(s), one or two groups selected from the group consisting of a formyl group, a C1-C6 alkyl group, a C2-C5 acyl group, and a C2-C5 alkoxycarbonyl group);

or a structure represented by formula (7):

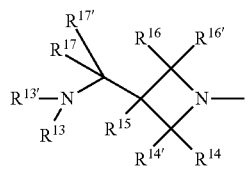

(7)

(wherein each of $R^{13}$, $R^{13'}$, $R^{14}$, $R^{14'}$, $R^{15}$, $R^{16}$, $R^{16'}$, $R^{17}$, and $R^{17'}$ represents a substituent on any of the aforementioned heterocyclic substituents represented by Z; more specifically, each of $R^{13}$ and $R^{13'}$ independently represents a hydrogen atom or a C1-C6 alkyl group, wherein the alkyl group may have, as a substituent(s), one or more groups selected from the group consisting of a halogen atom, a hydroxyl group, an amino group, a carbamoyl group, a C1-C6 alkylthio group, a C1-C6 alkoxy group, a C1-C6 alkylamino group, a C1-C6 halogenoalkyl group, and a C1-C6 aminoalkyl group;

each of $R^{14}$, $R^{14'}$, $R^{15}$, $R^{16}$, and $R^{16'}$ independently represents a hydrogen atom, a halogen atom, an amino group, a hydroxyl group, a carbamoyl group, a C1-C6 alkyl group, a C1-C6 alkylamino group, an aryl group, a heteroaryl group, a C1-C6 alkoxy group, a C1-C6 alkylthio group, a C1-C6 halogenoalkyl group, or a C1-C6 aminoalkyl group, wherein the aforementioned alkyl group, or the alkyl moiety of the alkylthio group, halogenoalkyl group, aminoalkyl group, or alkylamino group may have a cyclic structure, and may have, as a substituent(s), one or more atoms or groups selected from the group consisting of a halogen atom, a C1-C6 alkyl group, and a C1-C6 alkoxy group;

the amino moiety of the aforementioned amino group, alkylamino group, or aminoalkyl group may have, as a substituent(s), one or two C1-C6 alkyl groups (which may have a cyclic structure, and may have, as a substituent(s), one or more atoms or groups selected from the group consisting of a halogen atom, a hydroxyl group, a C1-C6 alkylthio group, and a C1-C6 alkoxy group) (when the amino moiety has two C1-C6 alkyl groups, they may be identical to or different from each other), and the amino moiety may be protected by a generally employed protective group; and each of $R^{17}$ and $R^{17'}$ independently represents a hydrogen atom, a C1-C6 alkyl group, an aryl group, or a heteroaryl group; the aryl group has 6 to 10 carbon atoms; and the heteroaryl group is a 5- or 6-membered ring, and may contain one to four hetero atoms arbitrarily selected from among a nitrogen atom, an oxygen atom, and a sulfur atom, wherein the aforementioned aryl group or heteroaryl group may have, as a substituent(s), one or more atoms or groups selected from the group consisting of a halogen atom, a hydroxyl group, a thiol group, an amino group, a nitro group, a cyano group, a carboxyl group, a carbamoyl group, a phenyl group, a C1-C6 alkyl group, a C1-C6 alkoxy group, a C1-C6 alkylthio group, a C2-C6 alkoxycarbonyl group, a C2-C5 acyl group, and a heteroaryl group (which is a 5- or 6-membered ring, and contains one to four hetero atoms arbitrarily selected from among a nitrogen atom, an oxygen atom, and a sulfur atom);

of these substituents, the alkyl group, alkoxy group, alkylthio group, alkoxycarbonyl group, acyl group, phenyl group, or heteroaryl group may have, as a substituent(s), one or more atoms or groups selected from the group consisting of a halogen atom, a hydroxyl group, a C1-C6 alkoxy group, and a C1-C6 alkylthio group, and the amino group may have, as a substituent(s), one or two groups selected from the group consisting of a formyl group, a C1-C6 alkyl group, a C2-C5 acyl group, and a C2-C5 alkoxycarbonyl group;

two substituents arbitrarily selected from among $R^{14}$, $R^{14'}$, $R^{15}$, $R^{16}$, $R^{16'}$, $R^{17}$, and $R^{17'}$ may together form a ring, and the thus-formed ring may contain, as a ring-constituting atom(s), one or more hetero atoms arbitrarily selected from among an oxygen atom, a nitrogen atom, and a sulfur atom; and the thus-formed ring may have, as a substituent(s), one or more atoms or groups selected from the group consisting of a halogen atom, a hydroxyl group, an amino group, a C1-C6 alkyl group, a C1-C6 alkoxy group, and a C1-C6 alkylthio group, and the amino group may have, as a substituent(s), one or two groups selected from the group consisting of a formyl group, a C1-C6 alkyl group, a C2-C5 acyl group, and a C2-C5 alkoxycarbonyl group).

Of these substituents, substituents having a structure represented by formula (3), (4), or (5) are preferred. Particularly, a substituent having a structure of formula (4) or (5) is preferred. When the quinolone skeleton is a pyridobenzoxazine skeleton, a substituent having a structure of formula (3) is preferred.

Specific examples of the substituent Z include, but are not limited to, substituents represented by the following structural formulas. Needless to say, when any of the substituents contains an asymmetric carbon atom, the substituent Z includes corresponding optically active substituents.

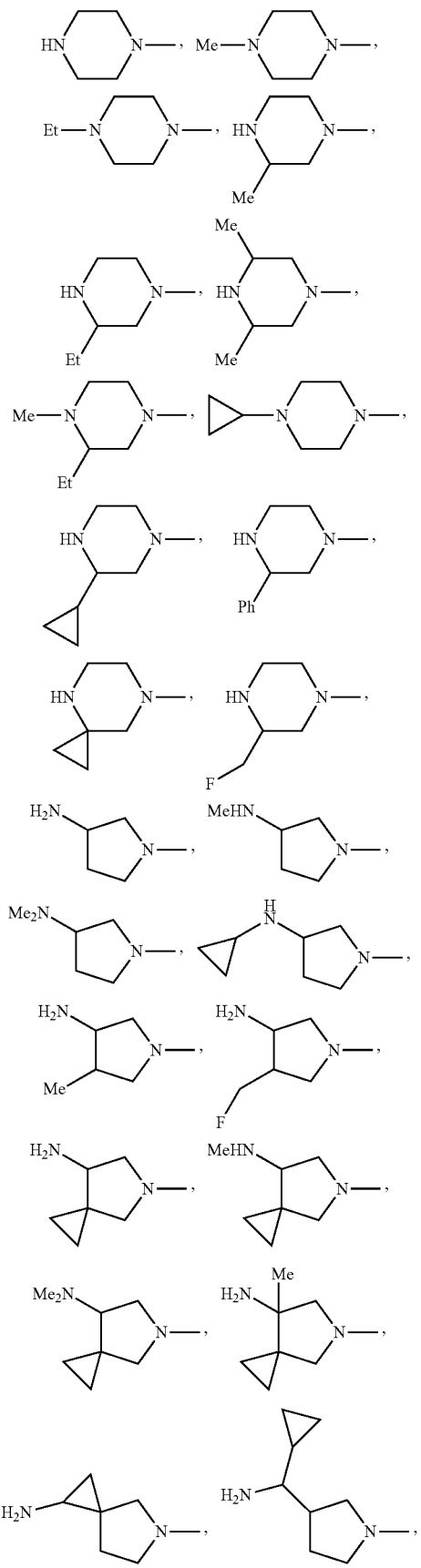

-continued

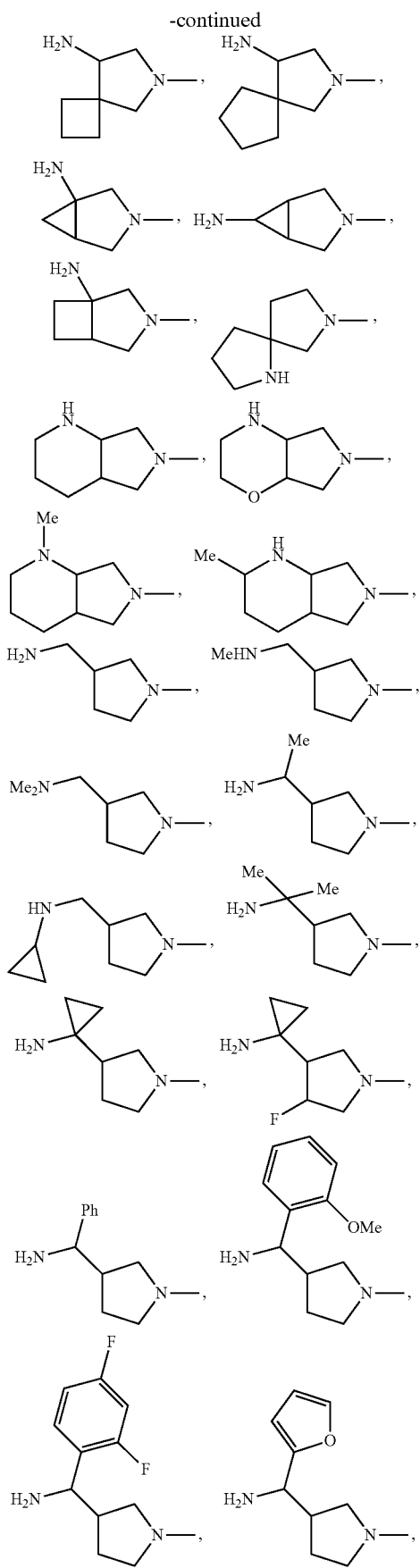
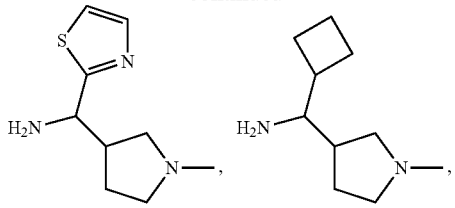

Specific examples of synthetic quinolone antibacterial compounds represented by formula (1) include levofloxacin, ofloxacin, sitafloxacin, (7-[3-(R)-(1-aminocyclopropyl)pyrrolidin-1-yl]-1-[2-(S)-fluoro-1-(R)-cyclopropyl]-1,4-dihydro-8-methoxy-4-oxoquinoline-3-carboxylic acid (compound (I)), (+)-7-[(7S)-7-amino-7-methyl-5-azaspiro[2.4]heptan-5-yl]-6-fluoro-1-[(1R,2S)-2-fluoro-1-cyclopropyl]-1,4-dihydro-8-methoxy-4-oxo-3-quinolinecarboxylic acid hemihydrate (compound (II)), ciprofloxacin, moxifloxacin, and trovafloxacin. When a quinolone compound is prepared into a lyophilized preparation through the method of the present invention, the quinolone compound may be in a free form or an adduct form (e.g., hydrate or salt).

When the synthetic quinolone antibacterial compound (1) of the present invention has a structure which allows presence of diastereomers, and when the compound is administered to a human or an animal subject, the compound to be administered is preferably formed of a single diastereomer. The expression "formed of a single diastereomer" include not only the case in which the compound is composed exclusively of a single diastereomer, but also the case in which the compound contains the other diastereomer in such an amount that does not affect physical constants and physiological activity. The same is applied to the case in which an antipode is present.

Next will be described the method for producing a lyophilized preparation of the present invention.

In the present invention, a lyophilized preparation is prepared from an aqueous solution for preparing the lyophilized preparation (starting solution) containing a synthetic quinolone antibacterial compound having a structure represented by formula (I) and a pH-adjusting agent as a sole additive. In the present invention, steps of lyophilization other than the annealing step may be performed according to a lyophilization method which is generally employed in the art.

Examples of pH-adjusting agents which may be employed in the present invention include inorganic acids such as hydrochloric acid, sulfuric acid, and phosphoric acid; inorganic acid salts such as sodium hydrogencarbonate, sodium carbonate, sodium hydrogenphosphate, sodium dihydrogenphosphate, trisodium phosphate, dipotassium phosphate, potassium dihydrogenphosphate, sodium sulfite, sodium hydrogensulfite, and sodium thiosulfate; organic acids such as acetic acid, lactic acid, succinic acid, maleic acid, tartaric acid, citric acid, ascorbic acid, salicylic acid, benzoic acid, methanesulfonic acid, and thioglycolic acid; organic acid esters such as ethyl lactate; organic acid salts such as sodium citrate, disodium citrate, sodium gluconate, calcium citrate, sodium lactate, sodium acetate, sodium pyrophosphate, sodium benzoate, sodium caprylate, and sodium thioglycolate; inorganic salts such as sodium hydroxide; and organic amine compounds such as monoethanolamine, diethanolamine, triethanolamine, ethylenediamine, meglumine, and trometamol. The pH of the aqueous solution is adjusted to 7 or less, preferably 6.5 or less, particularly preferably 2.5 to 6.0, from the viewpoint of solubility of the compound (1).

The compound (I) concentration of the aqueous solution for preparing a lyophilized preparation is preferably 10 mg/mL or more, more preferably 15 mg/mL or more, particularly preferably 20 mg/mL or more, from the viewpoint of formability of a lyophilized cake.

When, for example, compound (I) is employed, the aqueous solution for preparing a lyophilized preparation is preferably prepared according to a formulation shown in Table 1.

TABLE 1

Formulation of aqueous solution for preparing lyophilized preparation

| Purpose of use | Ingredient | Amount per vial (10 mL) |
|---|---|---|
| Main drug | Compound of formula (I) | 200 mg |
| pH-adjusting agent | Hydrochloric acid | Appropriate amount |
| pH-adjusting agent | Sodium hydroxide | (pH 2.5 to 4.5) |
| (Solvent) | (Water for injection) | (Total amount: 10 mL) |

In order to prepare a lyophilized preparation, at a first stage, the starting solution for the lyophilized preparation is cooled in a freezing step, to thereby yield a frozen product. The target temperature of the freezing step is set to a temperature equal to or lower than the so-called glass transition temperature of a frozen product of the compound (I)-containing aqueous solution. For example, a frozen product of an aqueous drug solution having a formulation shown in Table 1 has a glass transition temperature of around −15° C. Therefore, the target temperature of the freezing step is set to a temperature as low as −40° C., at which freezing is generally carried out in the art.

In the present invention, the target temperature of the freezing step is set to fall within a range of −20° C. to −40° C. When a frozen product obtained through freezing at −30° C. is subjected to a series of subsequent steps, an intended lyophilized preparation can be produced.

A characteristic feature of the lyophilized preparation production method of the present invention resides in that the temperature of the frozen product obtained through the freezing step is elevated to a certain level, and is maintained for a predetermined period of time (annealing step) (see the temperature profile of FIG. 1). This temperature profile indicates the setting temperature of an apparatus employed for lyophilization, and does not necessarily correspond to the temperature of individual containers (e.g., vials) accommodated in the apparatus. For example, conceivably, in the freezing step or a second drying step, the temperature of the containers in the apparatus reaches the level shown in the profile, whereas in a first drying step, the temperature of the containers in the apparatus is lowered to be equal to or lower than the setting level in accordance with sublimation of water.

The temperature of the annealing step may be determined on the basis of the glass transition temperature of the frozen product of the compound (1)-containing aqueous solution obtained through the freezing step. Specifically, the temperature of the frozen product is elevated to a level equal to or higher than the glass transition temperature thereof, and then maintained for a predetermined period of time. The glass transition temperature of the frozen product may be determined through, for example, DSC of the frozen product, and this DSC may be performed according to a generally employed method. The glass transition temperature of frozen products is varied in accordance with, for example, the compositional proportions of ingredients of starting solutions for the products. Therefore, different frozen products are subjected to DSC for determination of the glass transition temperature thereof.

Figure 5:
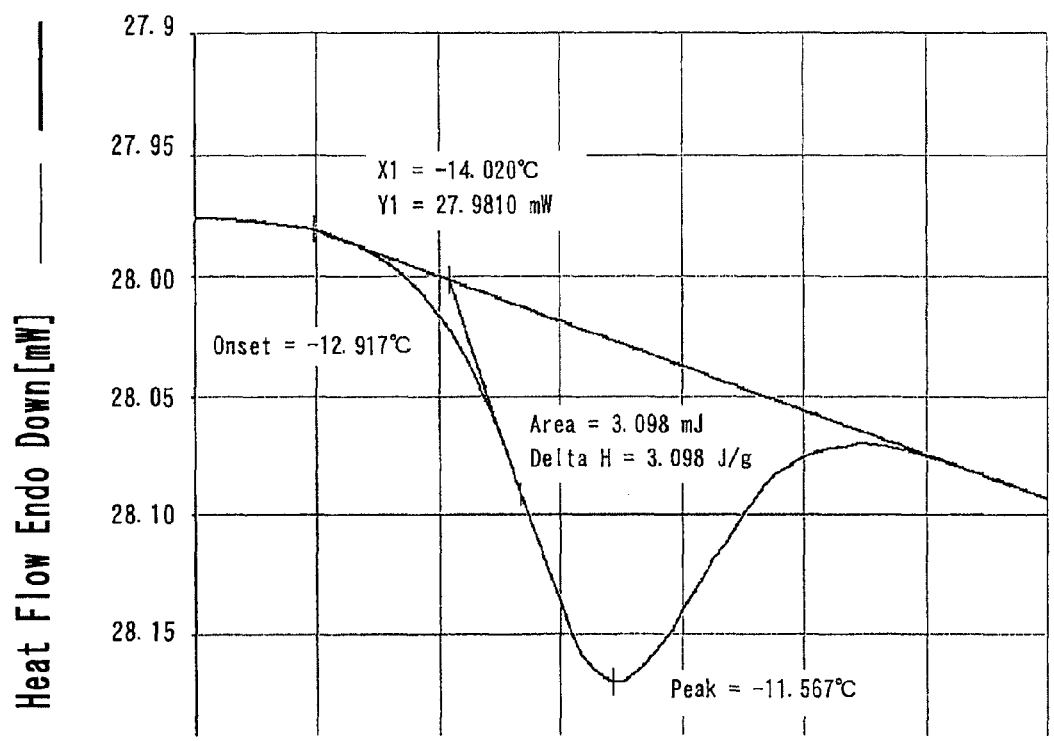
FIG. 5 shows DSC data of a frozen product of a compound (I)-containing aqueous solution (20 mg/mL) prepared through cooling to about −40° C.
Figure 6:
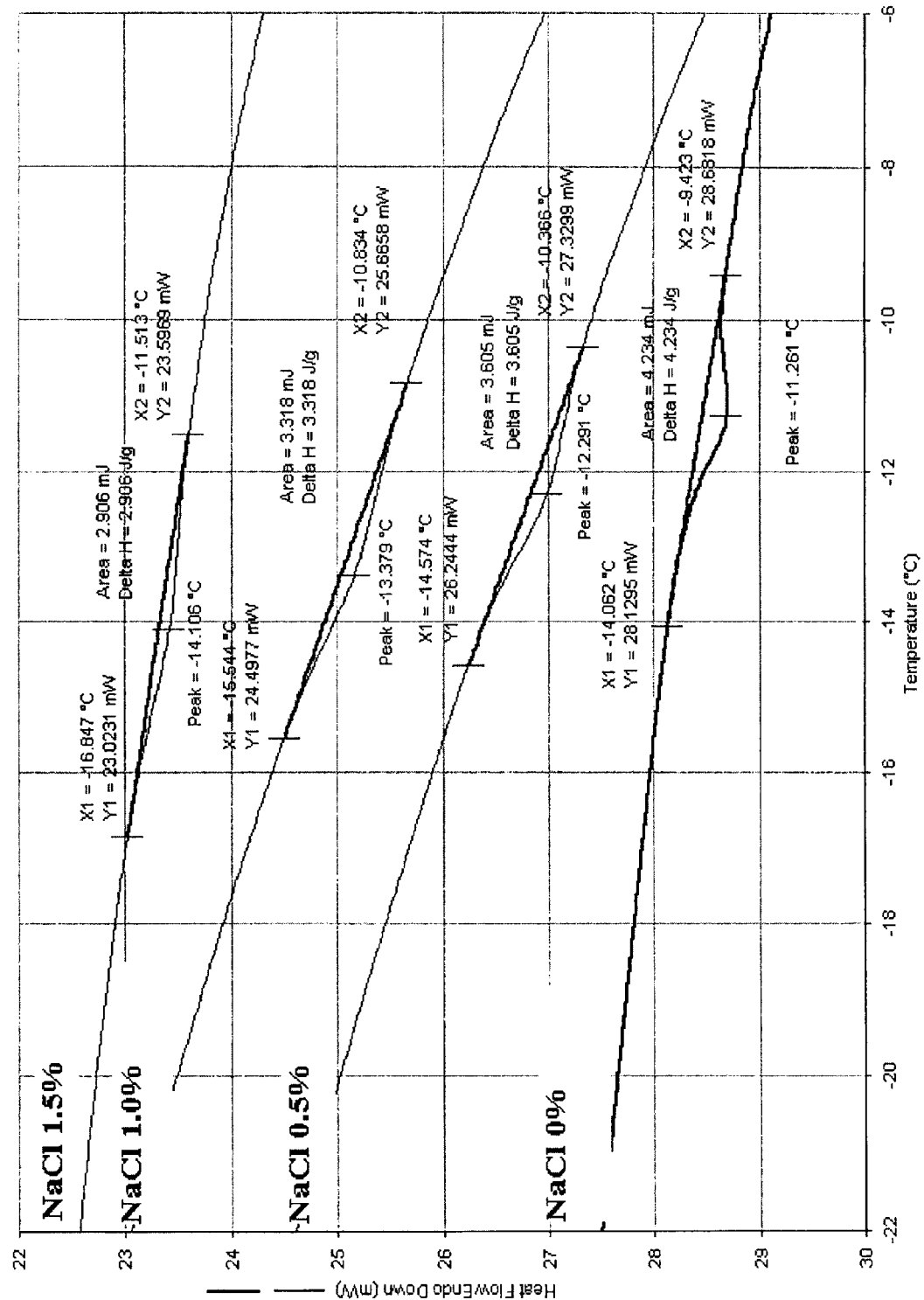
FIG. 6 shows different DSC data corresponding to different amounts of added sodium chloride.

For example, in the DSC chart of the frozen product containing compound (I) and pH-adjusting agents having a formulation shown in Table 1, the peak corresponding to the glass transition temperature of the frozen product rises at about −14.0° C. (FIG. 5). Therefore, when the frozen product is maintained within a temperature range of this temperature to a temperature at which the frozen product does not thaw, the resultant lyophilized preparation in the form of lyophilized cake exhibits improved reconstituting property. The peak itself was found to start at about −17° C. through DSC. Therefore, when the annealing step is performed at a temperature equal to or higher than this temperature, the annealing effect is expected to be attained.

Since a frozen product is required not to thaw in the annealing step, the maximum temperature of the annealing step is determined to a highest possible temperature at which the frozen product can be maintained in a frozen state. In general, an aqueous drug solution is considered to be maintained in a frozen state up to about 0° C. The higher the temperature of the annealing step, the higher the annealing effects. However, attention must be paid to the annealing temperature, since an excessively high annealing temperature causes thaw of a frozen product.

In the method of the present invention, the temperature at which the annealing step is performed is −20° C. to −2° C., more preferably −15° C. to −5° C.

The period of time for the annealing step; i.e., a period of time during which a frozen product is maintained at an elevated temperature, is adjusted to be equal to or longer than such a sufficient period that the entirety of the frozen product reaches a predetermined temperature. The period of time required for the annealing step varies depending on the annealing temperature (needless to say, the annealing time varies depending on other factors (e.g., the number of lyophilized preparations to be produced)). When the annealing temperature is nearer to the glass transition temperature of a frozen product; i.e., when the annealing temperature is lower, the annealing step requires a longer period of time, whereas when the annealing temperature is higher than the glass transition temperature, the time required for the annealing step is reduced.

In the method of the present invention, the period of time sufficient for maintaining a frozen product at an elevated temperature in the annealing step is generally about 15 minutes to about 48 hours, more preferably about 30 minutes to about 12 hours.

In the lyophilized preparation production method of the present invention, no particular limitation is imposed on the rate of lowering or elevating the temperature of a frozen product for cooling or heating thereof. It has already been elucidated that a lyophilized preparation is not particularly affected by such a temperature lowering/elevation rate, even when the rate is determined on the basis of factors (e.g., performance of an apparatus employed, and time for controlling a production process).

The annealing step is followed by a first drying step; i.e., a step of re-cooling the frozen product, and subjecting the frozen product to a treatment under reduced pressure (hereinafter the treatment may be referred to as a "reduced-pressure treatment"), thereby preparing a lyophilized preparation. The first drying step may be performed according to a generally employed lyophilization method. Specifically, the reduced-pressure treatment of the frozen product is initiated for lyophilization at the time when the temperature of the frozen product reaches a predetermined re-cooling temperature. Similar to the case of the cooling step before the annealing step, the target temperature of this re-cooling is set to be equal to or lower than the glass transition temperature of the frozen product, and is targeted to −40° C.; i.e., a temperature at which a lyophilized preparation is generally prepared. The target reduced pressure for the reduced-pressure treatment in the first drying step is 6 to 27 Pa, preferably 13 to 20 Pa.

The first drying step is performed under reduced pressure at a temperature equal to or lower than the glass transition point of the frozen product. This temperature corresponds to the target temperature of small-sized containers (e.g., vials) accommodated in the apparatus for lyophilization. In practice, the temperature of the apparatus may be set to a temperature equal to or higher than the glass transition temperature of the frozen product, since sublimation of water from the frozen product causes a decrease in temperature. In the present invention, the temperature of the apparatus is set to about 25° C. to about −15° C.

The period of time required for the first drying step, which varies depending on the amount of water which is sublimated, is about 16 hours to about 80 hours, more preferably 16 hours to 50 hours. As the water content of the product is reduced through sublimation, lowering in temperature is gradually suppressed, which results in initiation of elevation in temperature of the frozen product. Notably, the time at which the temperature of the frozen product starts to rise can be regarded as the point in time at which the first drying step is completed.

The first drying step is followed by a second drying step. In the second drying step, the temperature of the apparatus which has been set in the first drying step is elevated to a predetermined temperature of the second drying step, followed by maintaining for a predetermined period of time. The temperature of the second drying step is set to room temperature or higher (e.g., about 25° C. to about 45° C.), preferably 25° C. to 30° C. The period of time required for the second drying step is about 2 hours to about 20 hours, more preferably 3 hours to 15 hours. Similar to the case of the first drying step, the second drying step is performed under reduced pressure. In the second drying step, preferably, the vacuum level is increased so as to facilitate removal of water. The vacuum level is 0.5 Pa to 10 Pa, more preferably 1 Pa to 5 Pa.

In the method of the present invention for producing a lyophilized preparation, sterilization treatment, etc. may be performed according to a generally employed procedure.

EXAMPLES

The present invention will next be described in detail by way of examples, which, in any case, should not be construed as limiting the invention thereto.

Example 1

Lyophilized Preparation Containing a Drug Substance and a pH-adjusting Agent 1-mol/L Hydrochloric acid (1,400 mL) was added to water for injection (25 L). Compound (I) (600 g) was dissolved in the aqueous solution, and 1 mol/L hydrochloric acid was added thereto, to thereby attain a pH of 3.4. Water for injection was added to the resultant solution so that the compound (I) content was adjusted to 20 mg/mL, to thereby yield a starting solution for preparing a lyophilized preparation. The solution was dispensed and charged into small-sized containers (10 mL each), and was lyophilized through the below-described steps. After lyophilization, each container was tightly closed with a stopper.

[Lyophilization Step]

1) A container filled with the compound (I) solution was placed on a shelf of a lyophilizer set at 5° C.

2) The temperature of the shelf was lowered to −30° C. at a cooling rate of 0.15 degrees (° C.)/minute, followed by maintaining for 6 hours.

3) The temperature of the shelf was elevated to −10° C. at a temperature elevation rate of 0.5 degrees (° C.)/minute, followed by maintaining for 6 hours.

4) The temperature of the shelf was lowered to −40° C. at a cooling rate of 1.0 degree (° C.)/minute.

5) The temperature of the shelf was maintained at −40° C. for 3 hours or more.

6) Subsequently, a reduced-pressure treatment was initiated, and the temperature of the shelf was set to −5° C., followed by maintaining for 30 hours or more. During this maintenance period, vacuum level was maintained at 20 Pa.

7) After the temperature of the product contained in the container had reached −5° C. or higher, the temperature of the shelf was set to 25° C., followed by maintaining for 6 hours or more. During this maintenance period, vacuum level was maintained at 1 Pa.

Figure 2:
FIG. 2 shows the state observed about 30 seconds after addition of a liquid for reconstitution to a lyophilized preparation of compound (I) prepared through a lyophilization method without annealing step.
Figure 3:
FIG. 3 shows the state observed about 30 seconds after addition of a liquid for reconstitution to a lyophilized preparation of compound (I) prepared through a lyophilization method with an annealing step.
Figure 4:
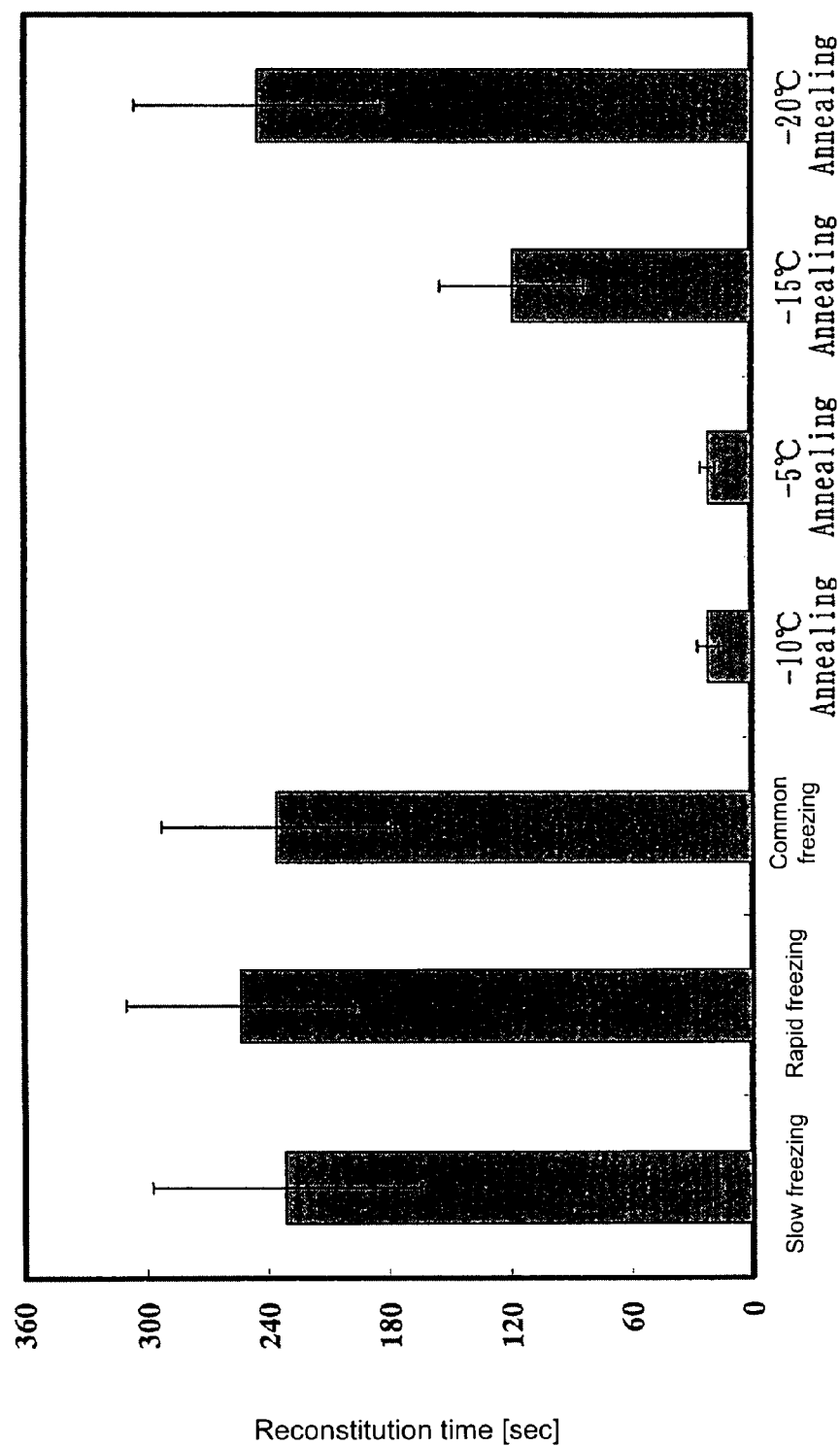
FIG. 4 shows the effect of an annealing step on the reconstitution time of a lyophilized preparation.

After a drug solution had been prepared in a manner similar to that described above, the solution was charged into a container and frozen under the conditions shown in Table 2, and then was lyophilized in a manner similar to that described above, followed by measurement of the time required for reconstitution (hereinafter the time may be referred to as a "reconstitution time"). The results are shown in FIG. 4. The state observed about 30 seconds after injection of a liquid for reconstitution is shown in FIG. 2 (method without annealing step) or FIG. 3 (method with an annealing step).

TABLE 2

| | Freezing conditions |
|---|---|
| Step | Shelf temperature setting program |
| Slow freezing | Cooling from 5.0° C. to −40° C. at 0.05° C./min |
| Rapid freezing | Loading of sample on shelf cooled to −40° C. |
| Common freezing | Cooling from 5.0° C. to −40° C. at 1.0° C./min |
| −10° C. Annealing | 5.0° C. → −30° C. (−0.15° C./min) → −10° C. (+0.5° C./min) → −40° C. (−1.0° C./min)[1] |
| −5° C. Annealing | 5.0° C. → −30° C. (−0.15° C./min) → −5° C. (+0.5° C./min) → −40° C. (−1.0° C./min)[2] |
| −15° C. Annealing | 5.0° C. → −30° C. (−0.15° C./min) → −15° C. (+0.5° C./min) → −40° C. (−1.0° C./min)[2] |
| −20° C. Annealing | 5.0° C. → −30° C. (−0.15° C./min) → −20° C. (+0.5° C./min) → −40° C. (−1.0° C./min)[2] |

Figure 7:
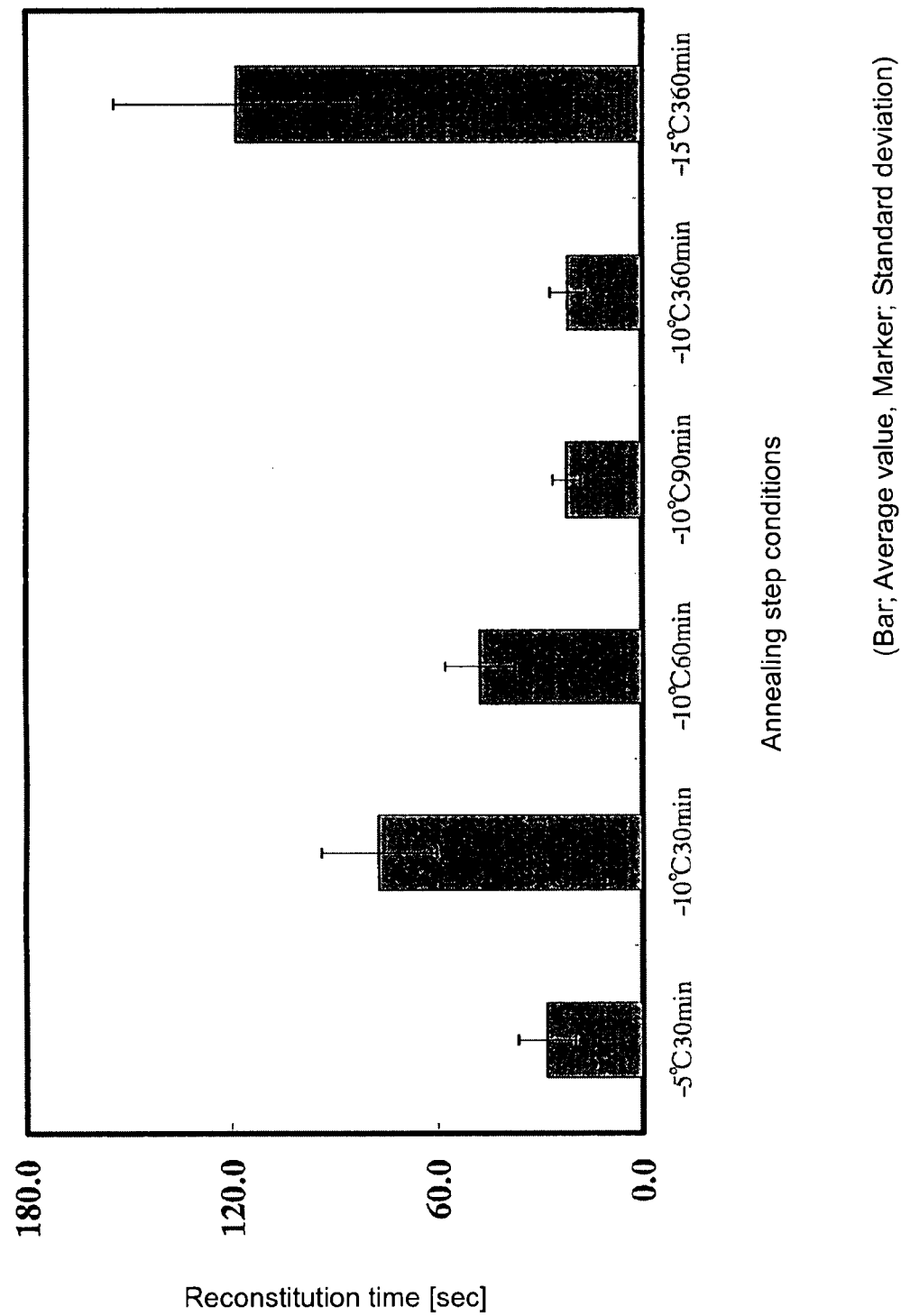
FIG. 7 shows different reconstitution times corresponding to different annealing conditions.

[1] Maintaining −30° C. for 360 minutes, and −10° C. for 30 to 360 minutes
[2] Maintaining −30° C. and the temperature elevation step for 360 minutes Lyophilization was performed under varied annealing conditions (e.g., temperature and maintenance time for an annealing step) as shown in Table 3. FIG. 7 shows the time required for reconstitution of the resultant lyophilized preparations. Reconstitution time was measured through the following procedure: after completion of lyophilization, water for injection was added to a vial in an amount equal to that of the liquid charged into the vial, followed by moderate shaking, and the time required for complete dissolution of the content of the vial was measured.

TABLE 3

| | Annealing and freezing conditions | |
|---|---|---|
| Step | Shelf temperature setting program | Annealing step maintenance time |
| −5° C. Annealing | 5.0° C. → −30° C. (−0.15° C./min) → −5° C. (+5° C./min) → −40° C. (−1.0° C./min) | 30 min |
| −10° C. Annealing | 5.0° C. → −30° C. (−0.15° C./min) → −10° C. (+0.5° C./min) → −40° C. (−1.0° C./min) | 30, 60, 90 & 360 min |
| −15° C. Annealing | 5.0° C. → −30° C. (−0.15° C./min) → −15° C. (+0.5° C./min) → −40° C. (−1.0° C./min) | 360 min |

Example 2

Figure 8:
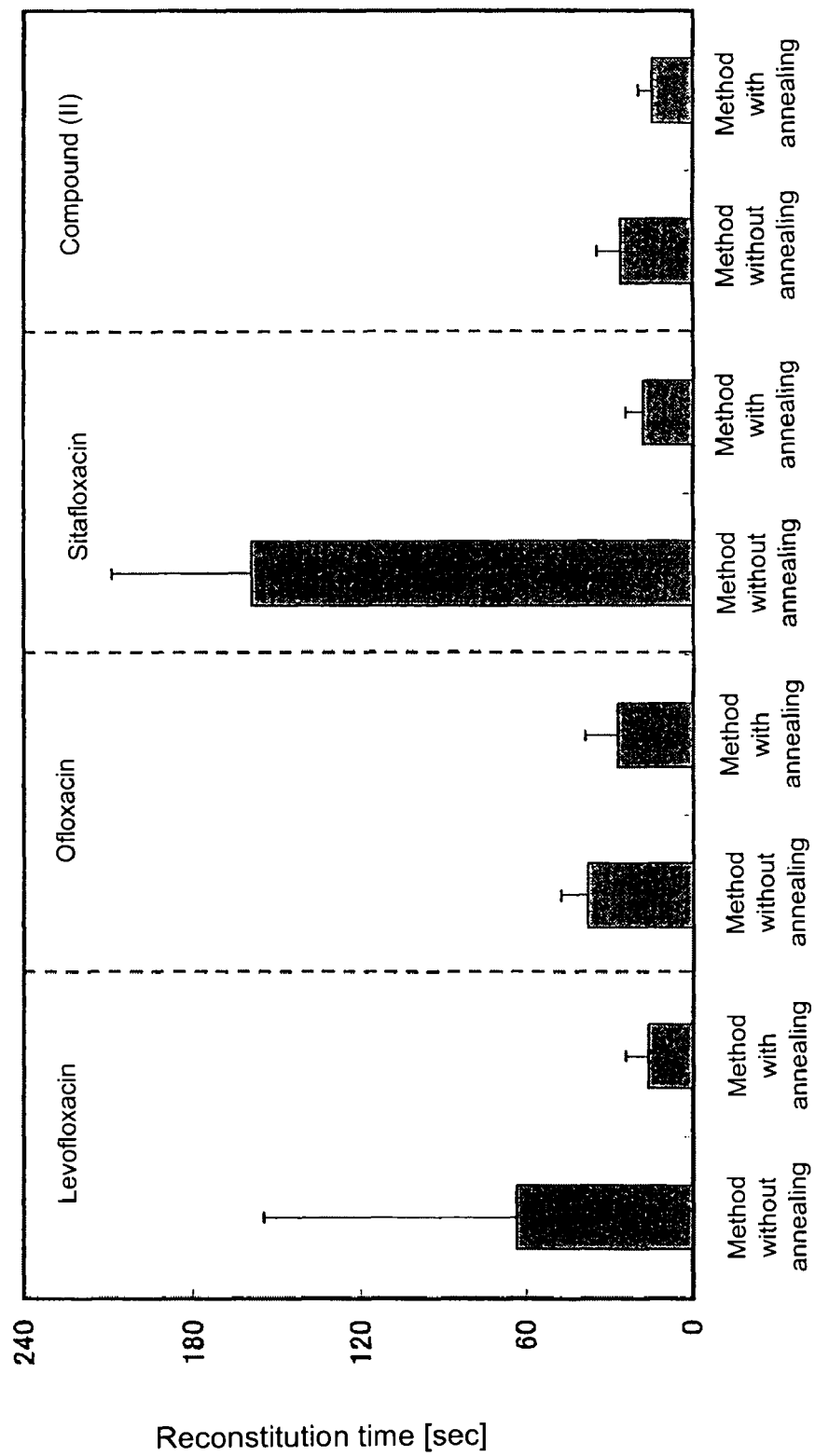
FIG. 8 shows the effect of an annealing step on the reconstitution time of a lyophilized preparation.

Lyophilized preparations were prepared from the following four synthetic quinolone antibacterial compounds: levofloxacin, ofloxacin, sitafloxacin, and compound (II), and the lyophilized preparations were evaluated in terms of the effect of an annealing step on improvement of reconstituting property. As a result, in the cases of the respective synthetic quinolone antibacterial compounds, lyophilized preparations prepared through a method with an annealing step were found to exhibit reduced reconstitution time (FIG. 8). The respective synthetic quinolone antibacterial compounds have the following structure.

1) Levofloxacin [(−)-(S)-9-fluoro-2,3-dihydro-3-methyl-10-(4-methyl-1-piperazinyl)-7-oxo-7H-pyrido[1,2,3-de][1,4]benzoxazine-6-carboxylic acid hemihydrate]

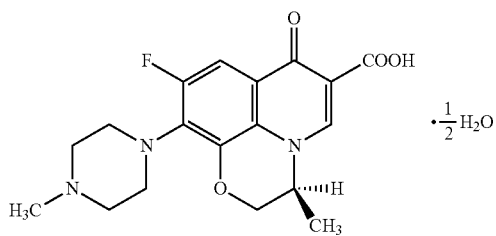

2) Ofloxacin [(±)-9-fluoro-2,3-dihydro-3-methyl-10-(4-methyl-1-piperazinyl)-7-oxo-7H-pyrido[1,2,3-de][1,4]benzoxazine-6-carboxylic acid]

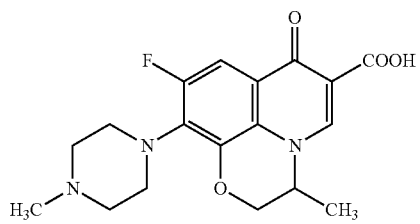

3) Sitafloxacin [(−)-7-[(7S)-7-amino-5-azaspiro[2.4]heptan-5-yl]-8-chloro-6-fluoro-1-[(1R,2S)-2-fluoro-1-cyclopropyl]-1,4-dihydro-4-oxo-3-quinolinecarboxylic acid sesquihydrate]

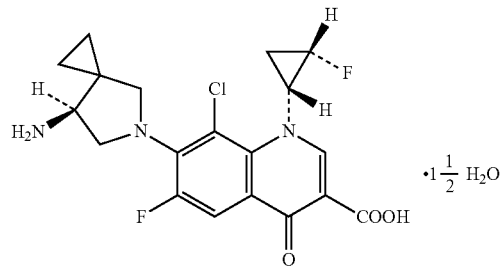

4) Compound (II) [(+)-7-[(7S)-7-amino-7-methyl-5-azaspiro[2.4]heptan-5-yl]-6-fluoro-1-[(1R,2S)-2-fluoro-1-cyclopropyl]-1,4-dihydro-8-methoxy-4-oxo-3-quinolinecarboxylic acid hemihydrate]

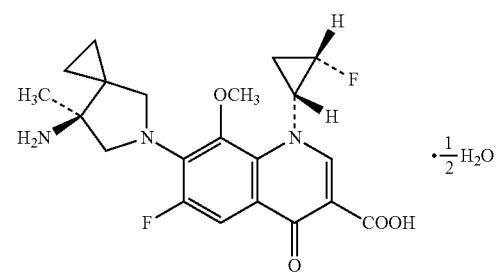

Compound (II) was produced through the following procedure.

(1) A mixture of tert-butyl acetoacetate (497 mL, 3.00 mol), 1,2-dibromoethane (310 mL, 3.60 mol), potassium carbonate (1.106 kg, 8.00 mol), and dimethylformamide (2.0 L) was stirred under heating in a water bath of 30° C. for 1.5 hours, a water bath of 60° C. for 3.5 hours, and a water bath of 30° C. for four days. The resultant reaction mixture was filtrated with Celite, and the residue was washed with diethyl ether (3.5 L). The filtrate and the liquid obtained through diethyl ether washing were added together to water (2 L), followed by separation of the organic layer. The aqueous layer was subjected to extraction with diethyl ether (2 L), and water (1 L) was added to the resultant aqueous layer, followed by extraction with diethyl ether (2 L). All the thus-obtained organic layers were mixed together, and the mixture was washed with 10% aqueous citric acid solution (2 L), water (2 L×3), and saturate brine (2 L×3), followed by drying over sodium sulfate anhydrate. After removal of the drying agent through filtration, the solvent was removed through evaporation under reduced pressure, and the resultant residue was subjected to distillation under reduced pressure, to thereby yield tert-butyl 1-acetyl-1-cyclopropanecarboxylate (371.8 g, distillate fraction at 10 mmHg and 72 to 78° C., 2.02 mol, 67%) as a colorless, transparent oil.

$^1$H-NMR (400 MHz, CDCl$_3$) δ ppm: 1.37-1.40 (4H,m), 1.49(9H,s), 2.44(3H,s).

(2) Tert-butyl 1-acetyl-1-cyclopropanecarboxylate (9.21 g, 50.0 mmol) was dissolved in 7 N ammonia/methanol solution (300 mL), and concentrated aqueous ammonia (90 mL), ammonium chloride (53.5 g, 1.00 mol), and sodium cyanide (4.90 g, 100.0 mmol) were added to the resultant solution under ice cooling, followed by stirring at room temperature for 18 hours. The solvent was removed under reduced pressure, and water (100 mL) was added to the resultant residue, followed by extraction with dichloromethane (300 mL+2×100 mL). The thus-obtained organic layers were mixed together, and the mixture was dried over sodium sulfate anhydrate. After removal of the drying agent through filtration, the solvent was removed through evaporation under reduced pressure, to thereby yield crude tert-butyl 1-(1-amino-1-cyanoethyl)-1-cyclopropanecarboxylate (10.15 g, 48.3 mmol, 97%) as a light brown oil. The thus-obtained crude product was employed for the subsequent reaction without being further purified.

$^1$H-NMR (400 MHz, CDCl$_3$) δ ppm: 1.02-1.12 (2H,m), 1.19-1.17 (2H,m), 1.48 (9H,s), 1.50 (3H,s), 2.13 (2H, brs);

MS (ESI) m/z: 155 (M−tBu)$^+$.

(3) An ethanol suspension (30 mL) of a Raney nickel catalyst (R-100, product of Nikko Rika) (10 mL) was added to an ethanol solution (50 mL) of tert-butyl 1-(1-amino-1-cyanoethyl)-1-cyclopropanecarboxylate (1.12 g, 5.30 mmol), followed by vigorous stirring in a hydrogen gas atmosphere at room temperature for 6 hours. The catalyst was removed through filtration with Celite, and the solvent was removed through evaporation under reduced pressure, to thereby yield crude tert-butyl 1-(1,2-diamino-1-methylethyl)-1-cyclopropanecarboxylate (0.84 g, 3.92 mmol, 74%) as a colorless, transparent oil. The thus-obtained crude product was employed for the subsequent reaction without being further purified.

MS (ESI) m/z: 215 (M+H)$^+$ (4) Crude tert-butyl 1-(1,2-diamino-1-methylethyl)-1-cyclopropanecarboxylate (0.82 g, 3.83 mmol) was dissolved in concentrated hydrochloric acid (5 mL) at room temperature, followed by stirring for 30 minutes at the same temperature. After addition of water to the resultant reaction mixture, the solvent was removed through evaporation under reduced pressure, followed by azeotropic distillation with ethanol (twice), to thereby yield crude 1-(1,2-diamino-1-methylethyl)-1-cyclopropanecarboxylic acid dihydrochloride (0.82 g, 3.55 mmol, 93%) as a light yellow foamy solid. The thus-obtained crude product was employed for the subsequent reaction without being further purified.

$^1$H-NMR (400 MHz, CD$_3$OD) δ ppm: 1.20-1.26 (1H,m), 1.28 (3H,s) 1.32-1.43 (2H,m), 1.58-1.62 (1H,m), 3.46 (1H,d, J=13.4 Hz), 3.80 (1H,d,J=13.4 Hz), MS (ESI) m/z: 159 (M+H)$^+$.

(5) 1,1,1,3,3,3-Hexamethyldisilazane (7.38 mL, 34.6 mmol) was added to an acetonitrile solution (70 mL) of crude 1-(1,2-diamino-1-methylethyl)-1-cyclopropanecarboxylic acid dihydrochloride (800 mg, 3.46 mmol), followed by refluxing in a nitrogen atmosphere under heating by means of an oil bath of 100° C. for 4 hours. The resultant reaction mixture was cooled to room temperature, and methanol (70 mL) was added thereto. Thereafter, the solvent was removed through evaporation under reduced pressure, to thereby yield crude 7-amino-7-methyl-5-azaspiro[2.4]heptan-4-one as a light brown gum-like solid.

MS (ESI) m/z: 141 (M+H)$^+$ 1,4-Dioxane (20 mL) and di-tert-butyl dicarbonate (1.528 g, 7.00 mmol) were added to the above-obtained crude 7-amino-7-methyl-5-azaspiro[2.4]heptan-4-one at room temperature, and the resultant mixture was stirred for 5 hours at the same temperature. Water (50 mL) was added to the resultant reaction mixture, followed by extraction with chloroform (100 mL+50 mL). Thereafter, the thus-obtained organic layers were mixed together, and the mixture was dried over sodium sulfate anhydrate. The drying agent was removed through filtration with a short silica gel column, and then the solvent was removed through evaporation under reduced pressure. Diethyl ether was added to the resultant residue, and the resultant suspension was filtrated, to thereby yield 7-(tert-butoxycarbonylamino)-7-methyl-5-azaspiro [2.4]heptan-4-one (502 mg, 2.09 mmol, two steps, 60%) as a white powder.

$^1$H-NMR (400 MHz, CDCl$_3$) δ ppm: 0.77-0.82 (1H,m), 0.94-1.04 (2H,m), 1.16-1.23 (1H,m), 1.28 (3H,s), 1.43 (9H, s), 3.29 (1H,d,J=10.3 Hz), 4.12 (1H,m), 4.60 (1H, brs), 5.82 (1H, brs), MS (ESI) m/z: 185 (M−tBu)$^+$.

(6) Sodium hydride (55%, mineral oil dispersion, 538 mg, 12.33 mmol) was added to a dimethylformamide solution (65 mL) of 7-(tert-butoxycarbonylamino)-7-methyl-5-azaspiro[2.4]heptan-4-one (3.12 g, 12.97 mmol) under ice cooling over five minutes, followed by stirring for 40 minutes at the same temperature. Thereafter, benzyl bromide (1.851 mL, 15.56 mmol) was added to the resultant mixture, followed by stirring at room temperature for 1.5 hours. The resultant reaction mixture was diluted with ethyl acetate (300 mL), and then washed with water (100 mL×2) and saturated brine (100 mL), followed by drying over sodium sulfate anhydrate. After removal of the drying agent through filtration, the solvent was removed through evaporation under reduced pressure, and the resultant residue was subjected to purification by silica gel column chromatography (hexane-ethyl acetate=9:1→4:1→2:1), to thereby yield 5-benzyl-7-(tert-butoxycarbonylamino)-7-methyl-5-azaspiro[2.4]heptan-4-one (4.20 g, 12.71 mmol, 98%) as a colorless, transparent gum-like solid.

$^1$H-NMR (400 MHz, CDCl$_3$) δ ppm: 0.76-0.81 (1H,m), 0.93-1.06 (2H,m), 1.21-1.29 (4H,m), 1.37 (9H,m), 3.14 (1H, d,J=10.3 Hz), 3.92-3.98 (1H,m), 4.44 (1H,d,J=15.1 Hz), 4.56 (1H,d,J=14.6 Hz), 4.56 (1H, brs), 7.22-7.33 (5H,m), MS (ESI) m/z: 331 (M+H)$^+$.

(7) The racemic mixture of 5-benzyl-7-(tert-butoxycarbonylamino)-7-methyl-5-azaspiro[2.4]heptan-4-one (2.254 g, 6.82 mmol), which had been obtained above in (6), was subjected to optical resolution by means of an optically active column (CHIRALPAK AD, 20 mmφ×250 mm, hexane-isopropyl alcohol=90:10, flow rate=20 mL/minute, 50 mg resolution per operation), to thereby yield (−)-5-benzyl-7-(tert-butoxycarbonylamino)-7-methyl-5-azaspiro [2.4]heptan-4-one (997 mg, 3.02 mmol, retention time=7.0 min, $[\alpha]_D^{25.1}$=−113.9° (c=0.180, chloroform) and (+)-5-benzyl-7-(tert-butoxycarbonylamino)-7-methyl-5-azaspiro[2.4]heptan-4-one (957 mg, 2.90 mmol, retention time=11.3 min, $[\alpha]_D^{25.1}$=+108.8° (c=0.249, chloroform)).

(8) Trifluoroacetic acid (7.5 mL) was added to a dichloromethane solution (15 mL) of (−)-5-benzyl-7-(tert-butoxycarbonylamino)-7-methyl-5-azaspiro[2.4]heptan-4-one (950 mg, 2.88 mmol) at room temperature, followed by stirring for 40 minutes at the same temperature. The solvent was removed through evaporation under reduced pressure, followed by azeotropic distillation with toluene (twice). Thereafter, saturated aqueous sodium hydrogencarbonate solution (30 mL) was added to the resultant product, followed by extraction with chloroform (100 mL+2×50 mL). The thus-obtained organic layers were mixed together, and the mixture was dried over sodium sulfate anhydrate. The drying agent was removed through filtration, and then the solvent was removed through evaporation under reduced pressure. The resultant residue was dissolved in tetrahydrofuran (30 mL), and lithium aluminum hydride (218 mg, 5.74 mmol) was added to the solution with stirring under ice cooling, followed by stirring for 1 hour at the same temperature. In addition, lithium aluminum hydride (109 mg, 2.87 mmol) was added to the resultant mixture, followed by stirring at room temperature for 2.5 hours. Thereafter, the mixture was ice-cooled, and water (0.31 mL), 15% aqueous sodium hydroxide solution (0.31 mL), and water (0.93 mL) were sequentially added to the ice-cooled mixture with care. The resultant mixture was stirred at room temperature overnight, and then dried over magnesium sulfate, followed by filtration with Celite. The filtrate was concentrated under reduced pressure, to thereby yield crude 7-amino-5-benzyl-7-methyl-5-azaspiro[2.4]heptane as a colorless, transparent oil. The thus-obtained crude product was employed for the subsequent reaction without being further purified.

$^1$H-NMR (400 MHz, CDCl$_3$) δ ppm: 0.37-0.45 (2H,m), 0.56-0.66 (2H,m), 0.96 (3H,s), 2.48 (1H,d,J=9.0 Hz), 2.55 (1H,d,J=8.8 Hz), 2.74 (2H,d,J=9.0 Hz), 3.59 (2H,s), 7.21-7.37 (5H,m), MS (ESI) m/z: 217 (M+H)$^+$.

The above-obtained crude 7-amino-5-benzyl-7-methyl-5-azaspiro[2.4]heptane was dissolved in dichloromethane (15 mL), and di-tert-butyl dicarbonate (1.255 g, 5.75 mmol) was added to the solution, followed by stirring at room temperature for 22 hours. The solvent was removed through evaporation under reduced pressure, and then the resultant residue was subjected to purification by silica gel column chromatography (chloroform-methanol-triethylamine=98:2:1→95:5:1), to thereby yield (−)-5-benzyl-7-(tert-butoxycarbonylamino)-7-methyl-5-azaspiro[2.4]heptane (586 mg, 1.852 mmol, three steps, 64%) as a colorless, transparent gum-like solid.

$^1$H-NMR (400 MHz, CDCl$_3$) δ ppm: 0.40-0.45 (1H,m), 0.50-0.55 (1H,m), 0.63-0.69 (1H,m), 0.80-0.85 (1H,m), 1.20 (3H,s), 1.43 (9H,s), 2.44 (1H,d,J=8.8 Hz), 2.59 (1H,d,J=9.5 Hz), 2.83 (1H,d,J=8.8 Hz), 3.33 (1H,m), 3.57 (1H,d,J=13.2 Hz), 3.68 (1H,d,J=13.2 Hz), 4.75 (1H, brs), 7.20-7.37 (5H, m), MS (ESI) m/z: 317 (M+H)$^+$.

$[α]_D^{25.1}$=−63.6° (c=0.129, chloroform)

(9) In a manner similar to that described above in (8), crude 7-amino-5-benzyl-7-methyl-5-azaspiro[2.4]heptane was produced, as a colorless, transparent oil, from (+)-5-benzyl-7-(tert-butoxycarbonylamino)-7-methyl-5-azaspiro[2.4]heptan-4-one (950 mg, 2.88 mmol).

$^1$H-NMR (400 MHz, CDCl$_3$) δ ppm: 0.37-0.45 (2H,m), 0.56-0.66 (2H,m), 0.96 (3H,s), 2.48 (1H,d,J=9.0 Hz), 2.55 (1H,d,J=8.8 Hz), 2.74 (2H,d,J=9.0 Hz), 3.59 (2H,s), 7.21-7.37 (5H,m), MS (ESI) m/z: 217 (M+H)$^+$.

In a manner similar to that described above in (8), (+)-5-benzyl-7-(tert-butoxycarbonylamino)-7-methyl-5-azaspiro[2.4]heptane (629 mg, 1.985 mmol, three steps, 69%) was produced, as a colorless, transparent gum-like solid, from the above-obtained crude 7-amino-5-benzyl-7-methyl-5-azaspiro[2.4]heptane.

$^1$H-NMR (400 MHz, CDCl$_3$) δ ppm: 0.40-0.45 (1H,m), 0.50-0.55 (1H,m), 0.63-0.69 (1H,m), 0.80-0.85 (1H,m), 1.20 (3H,s), 1.43 (9H,s), 2.44 (1H,d,J=8.8 Hz), 2.59 (1H,d,J=9.5 Hz), 2.83 (1H,d,J=8.8 Hz), 3.33 (1H,m), 3.57 (1H,d,J=13.2 Hz), 3.68 (1H,d,J=13.2 Hz), 4.75 (1H, brs), 7.20-7.37 (5H,m)

MS (ESI) m/z: 317 (M+H)$^+$.

$[α]_D^{25.1}$=+76.2° (c=0.290, chloroform)

(10) 10% Palladium carbon catalyst (M, about 50% hydrous, 349 mg) was added to a solution of (−)-5-benzyl-7-(tert-butoxycarbonylamino)-7-methyl-5-azaspiro[2.4]heptane (581 mg, 1.836 mmol) in methanol (40 mL), followed by stirring in a hydrogen gas atmosphere at room temperature for 2.5 hours. The catalyst was removed through filtration, and then the solvent was removed through evaporation under reduced pressure, to thereby yield 434 mg (quantitative) of crude (−)-7-(tert-butoxycarbonylamino)-7-methyl-5-azaspiro[2.4]heptane as a colorless, transparent gum-like solid.

$^1$H-NMR (400 MHz, CDCl$_3$) δ ppm: 0.38-0.43 (1H,m), 0.55-0.60 (2H,m), 0.74-0.80 (1H,m), 1.08 (3H,s), 1.44 (9H, s), 2.75 (1H,d,J=12.0 Hz), 2.77 (1H,d,J=11.5 Hz), 3.13 (1H, d,J=11.5 Hz), 3.75 (1H,brd,J=12.0 Hz), 4.44 (1H,brs), MS (ESI) m/z: 227 (M+H)$^+$.

$[α]_D^{25.1}$=−63.5° (c=0.277, chloroform).

(11) 10% Palladium carbon catalyst (M, about 50% hydrous, 376 mg) was added to a solution of (+)-5-benzyl-7-(tert-butoxycarbonylamino)-7-methyl-5-azaspiro[2.4]heptane (627 mg, 1.981 mmol) in methanol (40 mL), followed by stirring in a hydrogen gas atmosphere at room temperature for 5 hours. The catalyst was removed through filtration, and then the solvent was removed through evaporation under reduced pressure, to thereby yield 452 mg (quantitative) of crude (+)-7-(tert-butoxycarbonylamino)-7-methyl-5-azaspiro[2.4]heptane as a colorless, transparent gum-like solid.

$^1$H-NMR (400 MHz, CDCl$_3$) δ ppm: 0.38-0.43 (1H,m), 0.55-0.60 (2H,m), 0.74-0.80 (1H,m), 1.08 (3H,s), 1.44 (9H, s), 2.75 (1H,d,J=12.0 Hz), 2.77 (1H,d,J=11.5 Hz), 3.13 (1H, d,J=11.5 Hz), 3.75 (1H, brd, J=12.0 Hz), 4.44 (1H, brs), MS (ESI) m/z: 227 (M+H)$^+$.

$[α]_D^{25.1}$=+59.5° (c=0.185, chloroform).

(12) Crude (−)-7-(tert-butoxycarbonylamino)-7-methyl-5-azaspiro[2.4]heptane obtained above in (10) (434 mg, 1.836 mmol), 6,7-difluoro-1-[(1R,2S)-2-fluorocyclopropyl]-8-methoxy-1,4-dihydro-4-oxoquinoline-3-carboxylic acid-difluoroboron complex (663 mg, 1.836 mmol), and triethylamine (0.768 mL, 5.510 mmol) were dissolved in dimethyl sulfoxide (5 mL), followed by stirring under heating by means of an oil bath of 40° C. for 14 hours. A liquid mixture of ethanol and water (4:1) (50 mL) and triethylamine (5 mL) were added to the resultant reaction mixture, followed by refluxing under heating by means of an oil bath of 100° C. for 2 hours. The resultant reaction mixture was concentrated under reduced pressure, and the resultant residue was dissolved in ethyl acetate (200 mL), followed by washing with 10% aqueous citric acid solution (50 mL), water (50 mL×2), and saturated brine (50 mL). The organic layer was dried over anhydrous sodium sulfate, and then the solvent was removed through evaporation under reduced pressure, to thereby yield crude 7-[7-(tert-butoxycarbonylamino)-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid (870 mg, 1.676 mmol, 91%) as a yellow foamy solid.

$^1$H-NMR (400 MHz, CDCl$_3$) δ ppm: 0.55-0.60 (1H,m), 0.68-0.73 (1H,m), 0.74-0.80 (1H,m), 0.92-0.97 (1H,m), 1.22 (3H,s), 1.40 (9H,s), 1.43-1.59 (2H,m), 3.13 (1H,d,J=9.8 Hz), 3.60 (3H,s), 3.75 (1H,d,J=11.0, 3.7 Hz), 3.85 (1H,dt,J=10.2, 4.5 Hz), 4.18 (1H,d,J=10.0 Hz), 4.47 (1H,m), 4.62 (1H,s), 4.79-4.99 (1H,m), 7.83 (1H,d,J=13.7 Hz), 8.68 (1H,d,J=2.7 Hz), 14.88 (0.7H,brs), MS (ESI) m/z: 520 (M+H)$^+$.

$[α]_D^{25.1}$=−128.5° (c=1.240, chloroform).

(13) In a manner similar to that described above in (12), crude 7-[7-(tert-butoxycarbonylamino)-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid (1.00 g, 1.925 mmol, 97%) was produced, as a yellow foamy solid, from crude (+)-7-(tert-butoxycarbonylamino)-7-methyl-5-azaspiro[2.4]heptane obtained above in (11) (452 mg, 1.981 mmol) and 6,7-difluoro-1-[(1R,2S)-2-fluorocyclopropyl]-8-methoxy-1,4-dihydro-4-oxoquinoline-3-carboxylic acid-difluoroboron complex (715 mg, 1.981 mmol).

$^1$H-NMR (400 MHz, CDCl$_3$) δ ppm: 0.55-0.60 (1H,m), 0.68-0.80 (2H,m), 0.91-0.97 (1H,m), 1.21 (3H,s), 1.40 (9H, s), 1.53-1.68 (2H,m), 3.04 (1H,d,J=10.0 Hz), 3.61 (3H,s), 3.81 (1H,dd, J=10.7, 4.4 Hz), 3.87-3.93 (1H,m), 4.24 (1H,d, J=9.8 Hz), 4.46 (1H,m), 4.65-4.85 (2H,m), 7.83 (1H,d,J=13.4 Hz), 8.76 (1H,s), MS (ESI) m/z: 520 (M+H)$^+$.

$[\alpha]_D^{25.1}$+133.20° (c=2.230, chloroform).

(14) 7-[7-(tert-Butoxycarbonylamino)-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid obtained above in (12) (870 mg, 1.676 mmol) was dissolved in concentrated hydrochloric acid (10 mL) under ice cooling, followed by stirring at room temperature for 20 minutes. The resultant reaction mixture was washed with chloroform (20 mL×5). Saturated aqueous sodium hydroxide solution was added to the aqueous layer under ice cooling, to thereby attain a pH of 12.0, and then the pH was adjusted to 7.4 with hydrochloric acid, followed by extraction with a liquid mixture of chloroform and methanol (10:1) (200 mL×2) and an underlayer solution of chloroform, methanol, and water (7:3:1) (200 mL). The thus-obtained organic layers were mixed together, and the mixture was dried over anhydrous sodium sulfate, followed by removal of the solvent through evaporation under reduced pressure. The resultant residue was purified through recrystallization from ethanol, followed by drying under reduced pressure, to thereby yield compound (II) (644 mg, 1.535 mmol, 92%) as a light pink powder.

mp: 195 to 200° C.

$[\alpha]_D^{25.1}$=+40.8° (c=0.147, 0.1 N—NaOH);

$^1$H-NMR (400 MHz, 0.1 N—NaOD) δ ppm: 0.49-0.56 (2H,m), 0.67-0.76 (2H,m), 1.12 (3H,s), 1.43-1.64 (2H,m), 3.56 (3H,s), 3.59-3.71 (4H,m), 3.99-4.04 (1H,m), 4.80-5.03 (1H,m), 7.65 (1H,d,J=13.9 Hz), 8.45 (1H,s), Element analysis: as $C_{21}H_{23}F_2N_3O_4 \cdot 0.75EtOH \cdot 0.5H_2O$
Calcd.: C, 58.37; H, 6.20; F, 8.21; N, 9.08.
Found: C, 58.23; H, 5.99; F, 8.09; N, 9.02.

MS (EI) m/z: 419 (M$^+$);

IR (ATR): 2964, 2843, 1726, 1612, 1572, 1537, 1452, 1439, 1387, 1360, 1346, 1311, 1294, 1265, 1207 cm$^{-1}$.

[Preparation of Lyophilized Preparation]

Levofloxacin (8,000 mg as reduced to anhydride) was dissolved in water for injection (350 mL), and a pH-adjusting agent was added to the solution, to thereby attain a pH of 7. Water for injection was added to the resultant solution so that the levofloxacin content was 20 mg/mL. The solution was charged into containers (10 mL each), and was lyophilized. After lyophilization, the container was tightly closed with a cap.

[Lyophilization Method (with an Annealing Step)]

1) A container charged with a solution containing levofloxacin was placed on a shelf of a lyophilizer set at 5° C.

2) The temperature of the shelf was lowered to −30° C. at a cooling rate of 0.15 degrees (° C.)/minute, followed by maintaining for 3 hours.

3) The temperature of the shelf was elevated to −5° C. at a temperature elevation rate of 0.5 degrees (° C.)/minute, followed by maintaining for 2 hours.

4) The temperature of the shelf was lowered to −40° C. at a cooling rate of 1.0 degree (° C.)/minute.

5) The temperature of the shelf was maintained at −40° C. for 2 hours or more.

6) Subsequently, a reduced-pressure treatment was initiated, and the temperature of the shelf was set to 15° C., followed by maintaining for 30 hours or more. During this maintenance period, vacuum level was maintained at 20 Pa.

7) After the temperature of the product contained in the container had reached 15° C. or higher, the temperature of the shelf was set to 25° C., followed by maintaining for 6 hours or more. During this maintenance period, vacuum level was maintained at 1 Pa.

[Lyophilization Method without Annealing Step]

1) A container charged with a solution containing levofloxacin was placed on a shelf of a lyophilizer set at 5° C.

2) The temperature of the shelf was lowered to −40° C. at a cooling rate of 1.0 degree (° C.)/minute.

3) The temperature of the shelf was maintained at −40° C. for 2 hours or more.

4) Subsequently, a reduced-pressure treatment was initiated, and the temperature of the shelf was set to 15° C., followed by maintaining for 30 hours or more. During this maintenance period, vacuum level was maintained at 20 Pa.

5) After the temperature of the product contained in the container had reached 15° C. or higher, the temperature of the shelf was set to 25° C., followed by maintaining for 6 hours or more. During this maintenance period, vacuum level was maintained at 1 Pa.

Each of the three compounds other than levofloxacin was prepared into a solution under conditions shown in Table 4. The resultant solution was lyophilized in a manner similar to the case of levofloxacin, followed by tight capping.

[Reconstitution Time]

Water for injection (10 mL) was added to a vial, followed by moderate shaking, and the time required for complete dissolution of the content of the vial was measured.

TABLE 4

| Formulation of quinolone lyophilized preparation | | |
|---|---|---|
| Purpose of use | Ingredient | Amount per mL |
| [Levofloxacin] lyophilized preparation formulation | | |
| Main drug | Levofloxacin | 20.0 mg* |
| pH-adjusting agent | Hydrochloric acid Sodium hydroxide | pH 7 |
| Solvent | Water for injection | Total: 1 mL |
| [Ofloxacin] lyophilized preparation formulation | | |
| Main drug | Ofloxacin | 20.0 mg |
| pH-adjusting agent | Hydrochloric acid Sodium hydroxide | pH 5.6 |
| Solvent | Water for injection | Total: 1 mL |
| [Sitafloxacin] lyophilized preparation formulation | | |
| Main drug | Sitafloxacin | 20.0 mg |
| pH-adjusting agent | Hydrochloric acid Sodium hydroxide | pH 3.5 |
| Solvent | Water for injection | Total: 1 mL |
| [Compound II] lyophilized preparation formulation | | |
| Main drug | Compound II | 20.0 mg |
| pH-adjusting agent | Phosphoric acid Sodium hydroxide | pH 4 |
| Solvent | Water for injection | Total: 1 mL |

*As reduced to anhydride

The invention claimed is:

1. A method for producing a lyophilized preparation containing, as an active ingredient, a compound represented by the following formula (1):

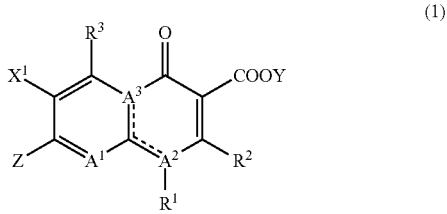

wherein $R^1$ represents a C1-C6 alkyl group, a C2-C6 alkenyl group, a C1-C6 halogenoalkyl group, a C3-C6 cycloalkyl group optionally substituted by a halogen atom, an aryl group optionally substituted by a halogen atom, a hydroxyl group, an amino group, a nitro group, a C1-C6 alkyl group, or a C1-C6 alkoxy group, a heteroaryl group optionally substituted by a halogen atom or a C1-C6 alkyl group, a C1-C6 alkoxy group, or a C1-C6 alkylamino group, $R^2$ represents a hydrogen atom or a C1-C6 alkylthio group, wherein $R^1$ and $R^2$ may be linked together to form a ring including a part of the quinolone skeleton, and the ring may contain a sulfur atom as a ring-constituting atom and optionally a C1-C6 alkyl group as a substituent, $R^3$ represents a hydrogen atom, an amino group optionally substituted by a formyl group, a C1-C6 alkyl group, or a C2-C5 acyl group, a thiol group, a halogenomethyl group, a C1-C6 alkyl group, a C2-C6 alkenyl group, a C2-C6 alkynyl group, or a C1-C6 alkoxy group;

$A^1$, $A^2$, $A^3$, and the carbon atom bonded thereto form a partial structure represented by the following formula:

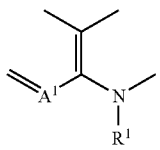

and $A^1$ represents a partial structure represented by formula (2):

wherein $X^2$ represents a hydrogen atom, an amino group, a halogen atom, a cyano group, a halogenomethyl group, a C1-C6 alkyl group, a C2-C6 alkenyl group, a C2-C6 alkynyl group or a C1-C6 alkoxy group, wherein the amino group is optionally substituted with a formyl group, a C1-C6 alkyl group or a C2-C5 acyl group, and wherein $X^2$ and $R^1$ may be linked together to form a ring including a part of the quinolone skeleton, and the ring optionally contains, as a ring-constituting atom, an oxygen atom, a nitrogen atom, or a sulfur atom and may have a C1-C6 alkyl group as a substituent;

$X^1$ represents a halogen atom or a hydrogen atom,

Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidyl group, a 5-alkyl-2-oxo-1,3-dioxol-4-ylmethyl group, a 3-acetoxy-2-oxobutyl group, a C1-C6 alkyl group, a C2-C7 alkoxymethyl group, or a phenylalkyl group consisting of a C1-C6 alkylene group and a phenyl group, Z represents a mono-, di-, or tricyclic heterocyclic substituent, wherein the heterocyclic substituent may be saturated or partially saturated and may contain one or more hetero atoms selected from the group consisting of a nitrogen atom, an oxygen atom, and a sulfur atom, or the heterocyclic substituent may have a bicyclo structure or a spirocyclic structure and may be substituted by one or more atoms or groups selected from the group consisting of a halogen atom, a hydroxyl group, an amino group, a carbamoyl group, a C1-C6 alkyl group, a C1-C6 halogenoalkyl group, an aryl group, a heteroaryl group, a C1-C6 alkoxy group, a C1-C6 alkylamino group, a C1-C6 alkylthio group, and a C1-C6 aminoalkyl group, wherein the method comprises, cooling an aqueous solution containing a compound represented by formula (1) and a pH-adjusting agent to yield a frozen product, elevating the temperature of the frozen product, and re-cooling the resultant to prepare the lyophilized preparation.

2. The method for producing a lyophilized preparation of claim 1, wherein $R^1$ is a cycloalkyl group or a halogenocycloalkyl group.

3. The method for producing a lyophilized preparation of claim 1 or 2, wherein each of $R^2$ and $R^3$ is a hydrogen atom.

4. The method for producing a lyophilized preparation of claim 1, wherein $X^2$ is a C1-C6 alkoxy group or a ring structure which contains, as a ring-constituting atom, an oxygen atom, a nitrogen atom, or a sulfur atom and which is formed from $X^2$, $R^1$, and a part of the quinolone skeleton.

5. The method for producing a lyophilized preparation of claim 1, wherein $X^1$ is a hydrogen atom or a fluorine atom.

6. The method for producing a lyophilized preparation of claim 1, wherein the compound represented by formula (1) is levofloxacin, ofloxacin, sitafloxacin, (7-[3-(R)-(1-aminocyclopropyl)pyrrolidin-1-yl]-1-[2-(S)-fluoro-1-(R)-cyclopropyl]-1,4-dihydro-8-methoxy-4-oxoquinoline-3-carboxylic acid, (+)-7-[(7S)-7-amino-7-methyl-5-azaspiro[2.4]heptan-5-yl]-6-fluoro-1-[(1R,2S)-2-fluoro-1-cyclopropyl]-1,4-dihydro-8-methoxy-4-oxo-3-quinolinecarboxylic acid hemihydrate, ciprofloxacin, moxifloxacin, or trovafloxacin.

7. The method for producing a lyophilized preparation of claim 1, wherein the temperature of the frozen product is elevated to the glass transition temperature of the frozen product to the freezing temperature of the aqueous solution.

8. The method for producing a lyophilized preparation of claim 1, wherein the temperature of the frozen product is elevated to a temperature falling within a range of −20° C. to −2° C.

9. The method for producing a lyophilized preparation of claim 1, wherein the temperature of the frozen product is elevated to a temperature falling within a range of −15° C. to −5° C.

10. A method for producing a lyophilized preparation containing, as an active ingredient, a compound represented by the following formula (1):

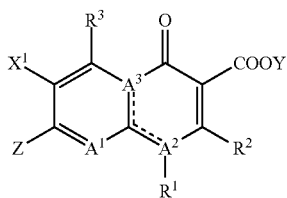

(1)

wherein R¹ represents a C1-C6 alkyl group, a C2-C6 alkenyl group, a C1-C6 halogenoalkyl group, a C3-C6 cycloalkyl group optionally substituted by a halogen atom, an aryl group optionally substituted by a halogen atom, a hydroxyl group, an amino group, a nitro group, a C1-C6 alkyl group, or a C1-C6 alkoxy group, a heteroaryl group optionally substituted by a halogen atom or a C1-C6 alkyl group, a C1-C6 alkoxy group, or a C1-C6 alkylamino group, R² represents a hydrogen atom or a C1-C6 alkylthio group, wherein R¹ and R² may be linked together to form a ring including a part of the quinolone skeleton, and the ring may contain a sulfur atom as a ring-constituting atom and may have a C1-C6 alkyl group as a substituent, R³ represents a hydrogen atom, an amino group optionally substituted by a formyl group, a C1-C6 alkyl group, or a C2-C5 acyl group, a thiol group, a halogenomethyl group, a C1-C6 alkyl group, a C2-C6 alkenyl group, a C2-C6 alkynyl group, or a C1-C6 alkoxy group;

A¹, A², A³, and the carbon atom bonded thereto form a partial structure represented by the following formula:

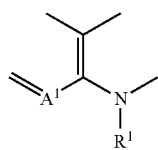

and A¹ represents a partial structure represented by formula (2):

(2)

wherein X² represents a hydrogen atom, an amino group, a halogen atom, a cyano group, a halogenomethyl group, a C1-C6 alkyl group, a C2-C6 alkenyl group, a C2-C6 alkynyl group or a C1-C6 alkoxy group, wherein the amino group is optionally substituted with a formyl group, a C1-C6 alkyl group or a C2-C5 acyl group, and wherein X² and R¹ may be linked together to form a ring including a part of the quinolone skeleton, and the ring optionally contains, as a ring-constituting atom, an oxygen atom, a nitrogen atom, or a sulfur atom and may have a C1-C6 alkyl group as a substituent X¹ represents a halogen atom or a hydrogen atom, Y represents a hydrogen atom, a phenyl group. an acetoxymethyl group, a pivaloyloxymethyl group, an ethoxycarbonyl group, a choline group, a dimethylaminoethyl group, a 5-indanyl group, a phthalidyl group, a 5-alkyl-2-oxo-1,3-dioxol-4-ylmethyl group, a 3-acetoxy-2-oxobutyl group, a C1-C6 alkyl group, a C2-C7 alkoxymethyl group, or a phenylalkyl group consisting of a C1-C6 alkylene group and a phenyl group, Z represents a mono-, di-, or tricyclic heterocyclic substituent, wherein the heterocyclic substituent may be saturated or partially saturated and may contain one or more hetero atoms selected from the group consisting of a nitrogen atom, an oxygen atom, and a sulfur atom, or the heterocyclic substituent may have a bicyclo structure or a spirocyclic structure and may be substituted by one or more atoms or groups selected from the group consisting of a halogen atom, a hydroxyl group, an amino group. a carbamoyl group, a C1-C6 alkyl group, a C1-C6 halogenoalkyl group, an aryl group, a heteroaryl group, a C1-C6 alkoxy group, a C1-C6 alkylamino group, a C1-C6 alkylthio group, and a C1-C6 aminoalkyl group, wherein the method comprises subjecting an aqueous solution containing a compound represented by formula (1) and a pH-adjusting agent to the following in sequence:

1) cooling the aqueous solution to yield a frozen product;

2) annealing by elevating the temperature of the frozen product; and 3) re-cooling the resultant product in 2) to prepare the lyophilized preparation.

wherein the method comprises subjecting an aqueous solution containing a compound represented by formula (1) and a pH-adjusting agent to the following in sequence:

1) cooling the aqueous solution to yield a frozen product;

2) annealing by elevating the temperature of the frozen product; and 3) re-cooling the resultant product in 2) to prepare the lyophilized preparation.

11. The method for producing a lyophilized preparation of claim 10, wherein the annealing is performed at a temperature ranging from the glass transition temperature of the frozen product to the freezing temperature of the aqueous solution.

12. The method for producing a lyophilized preparation of claim 10, wherein the annealing is performed at a temperature falling within a range of −20° C. to −2° C.

13. The method for producing a lyophilized preparation of claim 10, wherein the annealing is performed at a temperature falling within a range of −15° C. to −5° C.

* * * * *

UNITED STATES PATENT AND TRADEMARK OFFICE
CERTIFICATE OF CORRECTION

PATENT NO. : 8,129,533 B2
APPLICATION NO. : 12/067826
DATED : March 6, 2012
INVENTOR(S) : Norihiro Nishimoto Page 1 of 1

It is certified that error appears in the above-identified patent and that said Letters Patent is hereby corrected as shown below:

On the title page, Item (73), the Assignee's name is incorrect. Item (73) should read:

-- (73)   Assignee: Daiichi Sankyo Company, Limited,
Tokyo (JP) --

Signed and Sealed this
First Day of May, 2012

David J. Kappos
*Director of the United States Patent and Trademark Office*

UNITED STATES PATENT AND TRADEMARK OFFICE
CERTIFICATE OF CORRECTION

PATENT NO. : 8,129,533 B2
APPLICATION NO. : 12/067826
DATED : March 6, 2012
INVENTOR(S) : Norihiro Nishimoto It is certified that error appears in the above-identified patent and that said Letters Patent is hereby corrected as shown below:

Column 34, deletes lines 36-45.

Signed and Sealed this
Twelfth Day of June, 2012

David J. Kappos
*Director of the United States Patent and Trademark Office*